US009532883B2

(12) United States Patent
McLuen et al.

(10) Patent No.: US 9,532,883 B2
(45) Date of Patent: Jan. 3, 2017

(54) BONE FUSION DEVICE

(71) Applicant: Neuropro Technologies, INC., Modesto, CA (US)

(72) Inventors: Gary R. McLuen, Port Townsend, WA (US); Daniel R. Baker, Seattle, WA (US); Benjamin J. Remington, Modesto, CA (US)

(73) Assignee: Neuropro Technologies, Inc., Modesto, CA (US)

( * ) Notice: Subject to any disclaimer, the term of this patent is extended or adjusted under 35 U.S.C. 154(b) by 0 days.

(21) Appl. No.: 13/838,119

(22) Filed: Mar. 15, 2013

(65) Prior Publication Data

US 2013/0274883 A1    Oct. 17, 2013

Related U.S. Application Data

(60) Provisional application No. 61/624,155, filed on Apr. 13, 2012.

(51) Int. Cl.
*A61F 2/44* (2006.01)
*A61F 2/46* (2006.01)
(Continued)

(52) U.S. Cl.
CPC .............. *A61F 2/447* (2013.01); *A61F 2/441* (2013.01); *A61F 2/4657* (2013.01); *A61B 90/03* (2016.02); *A61B 2017/00398* (2013.01); *A61B 2017/0256* (2013.01); *A61B 2090/032* (2016.02); *A61B 2090/061* (2016.02); *A61B 2090/065* (2016.02); *A61B 2090/0807* (2016.02);
(Continued)

(58) Field of Classification Search
CPC .......... A61F 2/44; A61F 2/4455; A61F 2/447; A61F 2/4611; A61F 2002/30579; A61F 2002/30601; A61F 2002/4475
USPC ............................................ 623/17.11–17.17
See application file for complete search history.

(56) References Cited

U.S. PATENT DOCUMENTS 4,309,777 A    1/1982 Patil
4,863,476 A    9/1989 Shepperd
(Continued)

FOREIGN PATENT DOCUMENTS

WO    2006134262 A1    12/2006
WO    2008086276 A2    7/2008
WO    2013023096 A1    2/2013

OTHER PUBLICATIONS

Search Report from European Application No. EP13797446.

*Primary Examiner* — Eduardo C Robert
*Assistant Examiner* — Michelle C Eckman
(74) *Attorney, Agent, or Firm* — Haverstock & Owens LLP

(57) ABSTRACT

A bone fusion device for insertion between bones that are to be fused together, such as, for example, the vertebrae of a spinal column. The bone fusion device comprises at least one extendable tab and one or more tab extension assemblies. Each tab extension assembly is able to be adjusted in order to individually control the extension or contraction of a side of the tab thereby enabling adjustment of the height and/or angle of the tab with respect to the body of the bone fusion device. Each tab extension assembly is able to be individually adjusted such that the side controlled by each assembly is raised or lowered until the desired tab angle is achieved. The tab is advantageously positioned and angled to correspond to the vertebrae to help brace the device until the bone has fused.

26 Claims, 24 Drawing Sheets

(51) Int. Cl.
*A61F 2/28* (2006.01)
*A61F 2/30* (2006.01)
*A61B 17/00* (2006.01)
*A61B 17/02* (2006.01)

(52) U.S. Cl.
CPC ........... *A61F 2/4465* (2013.01); *A61F 2/4601* (2013.01); *A61F 2002/2839* (2013.01); *A61F 2002/30522* (2013.01); *A61F 2002/30525* (2013.01); *A61F 2002/30538* (2013.01); *A61F 2002/30556* (2013.01); *A61F 2002/30579* (2013.01); *A61F 2002/30581* (2013.01); *A61F 2002/30601* (2013.01); *A61F 2002/30617* (2013.01); *A61F 2002/448* (2013.01); *A61F 2002/4661* (2013.01); *A61F 2002/4666* (2013.01)

(56) References Cited

U.S. PATENT DOCUMENTS

| | | | | |
|---|---|---|---|---|
| 4,961,740 | A | 10/1990 | Ray et al. | |
| 5,015,247 | A | 5/1991 | Michelson | |
| 5,059,193 | A | 10/1991 | Kuslich | |
| 5,123,926 | A | 6/1992 | Pisharodi | |
| 5,171,278 | A | 12/1992 | Pisharodi | |
| 5,443,514 | A | 8/1995 | Steffee | |
| 5,458,642 | A | 10/1995 | Beer et al. | |
| 5,522,899 | A | 6/1996 | Michelson | |
| 5,653,763 | A | 8/1997 | Errico et al. | |
| 5,658,335 | A | 8/1997 | Allen | |
| 5,665,122 | A | 9/1997 | Kambin | |
| 5,693,100 | A | 12/1997 | Pisharodi | |
| 5,702,391 | A | 12/1997 | Lin | |
| 5,716,415 | A | 2/1998 | Steffee | |
| 5,782,832 | A | 7/1998 | Larsen et al. | |
| 5,800,547 | A | 9/1998 | Schafer et al. | |
| 5,800,550 | A | 9/1998 | Sertich | |
| 5,827,328 | A | 10/1998 | Buttermann | |
| 5,865,848 | A | 2/1999 | Baker | |
| 5,885,287 | A | 3/1999 | Bagby | |
| 5,928,284 | A | 7/1999 | Mehdizadeh | |
| 5,980,522 | A | 11/1999 | Koros et al. | |
| 6,045,579 | A | 4/2000 | Hochshuler et al. | |
| 6,080,158 | A | 6/2000 | Lin | |
| 6,080,193 | A | 6/2000 | Hochshuler et al. | |
| 6,102,949 | A | 8/2000 | Biedermann et al. | |
| 6,102,950 | A | 8/2000 | Vaccaro | |
| 6,117,174 | A | 9/2000 | Nolan | |
| 6,129,763 | A | 10/2000 | Chauvin et al. | |
| 6,156,067 | A | 12/2000 | Bryan et al. | |
| 6,159,244 | A | 12/2000 | Suddaby | |
| 6,174,334 | B1 | 1/2001 | Suddaby | |
| 6,176,881 | B1 | 1/2001 | Schar et al. | |
| 6,176,882 | B1 * | 1/2001 | Biedermann et al. | 623/17.15 |
| 6,179,873 | B1 | 1/2001 | Zientek | |
| 6,183,517 | B1 | 2/2001 | Suddaby | |
| 6,190,414 | B1 * | 2/2001 | Young et al. | 623/17.15 |
| 6,231,609 | B1 | 5/2001 | Mehdizadeh | |
| 6,342,074 | B1 | 1/2002 | Simpson | |
| 6,371,968 | B1 | 4/2002 | Kogasaka et al. | |
| 6,371,987 | B1 | 4/2002 | Weiland et al. | |
| 6,375,655 | B1 | 4/2002 | Zdeblick et al. | |
| 6,375,683 | B1 | 4/2002 | Crozet et al. | |
| 6,409,766 | B1 | 6/2002 | Brett | |
| 6,419,705 | B1 | 7/2002 | Erickson | |
| 6,436,140 | B1 | 8/2002 | Liu et al. | |
| 6,443,989 | B1 | 9/2002 | Jackson | |
| 6,454,806 | B1 * | 9/2002 | Cohen et al. | 623/17.15 |
| 6,454,807 | B1 | 9/2002 | Jackson | |
| 6,464,727 | B1 | 10/2002 | Sharkey et al. | |
| 6,488,710 | B2 | 12/2002 | Besselink | |
| 6,491,695 | B1 | 12/2002 | Roggenbuck | |
| 6,527,803 | B1 | 3/2003 | Crozet et al. | |
| 6,562,041 | B1 | 5/2003 | Yonemura et al. | |
| 6,572,619 | B2 | 6/2003 | Santilli | |
| 6,572,653 | B2 | 6/2003 | Simonson | |
| 6,576,016 | B1 | 6/2003 | Hochshuler et al. | |
| 6,582,431 | B1 | 6/2003 | Ray | |
| 6,582,467 | B1 | 6/2003 | Teitelbaum et al. | |
| 6,595,995 | B2 | 7/2003 | Zdeblick et al. | |
| 6,613,091 | B1 | 9/2003 | Zdeblick et al. | |
| 6,645,249 | B2 | 11/2003 | Ralph et al. | |
| 6,652,584 | B2 | 11/2003 | Michelson | |
| 6,666,888 | B1 | 12/2003 | Jackson | |
| 6,685,742 | B1 | 2/2004 | Jackson | |
| 6,706,070 | B1 | 3/2004 | Wagner et al. | |
| 6,709,458 | B2 | 3/2004 | Michelson | |
| 6,723,126 | B1 * | 4/2004 | Berry | 623/17.11 |
| 6,723,128 | B2 | 4/2004 | Uk | |
| 6,746,454 | B2 | 6/2004 | Winterbottom et al. | |
| 6,767,367 | B1 | 7/2004 | Michelson | |
| 6,770,095 | B2 | 8/2004 | Grinberg et al. | |
| 6,770,096 | B2 | 8/2004 | Bolger et al. | |
| 6,808,537 | B2 | 10/2004 | Michelson | |
| 6,821,298 | B1 | 11/2004 | Jackson | |
| 6,830,589 | B2 | 12/2004 | Erickson | |
| 6,835,206 | B2 | 12/2004 | Jackson | |
| 6,902,568 | B2 | 6/2005 | Serhan | |
| 6,923,830 | B2 | 8/2005 | Michelson | |
| 6,962,606 | B2 | 11/2005 | Michelson | |
| 6,979,353 | B2 | 12/2005 | Bresina | |
| 6,989,011 | B2 | 1/2006 | Paul et al. | |
| 7,008,453 | B1 | 3/2006 | Michelson | |
| 7,018,415 | B1 * | 3/2006 | McKay | 623/17.15 |
| 7,041,309 | B2 | 5/2006 | Remington et al. | |
| 7,048,763 | B2 | 5/2006 | Ralph et al. | |
| 7,094,257 | B2 | 8/2006 | Mujwid et al. | |
| 7,108,862 | B2 | 9/2006 | Remington et al. | |
| 7,118,598 | B2 | 10/2006 | Michelson | |
| 7,128,760 | B2 | 10/2006 | Michelson | |
| 7,166,130 | B2 | 1/2007 | Ferree | |
| 7,211,112 | B2 | 5/2007 | Baynham et | |
| 7,217,291 | B2 * | 5/2007 | Zucherman et al. | 623/17.15 |
| 7,217,293 | B2 | 5/2007 | Branch, Jr. | |
| 7,220,280 | B2 | 5/2007 | Kast et al. | |
| 7,235,103 | B2 | 6/2007 | Rivin | |
| 7,238,186 | B2 | 7/2007 | Zdeblick et al. | |
| 7,331,994 | B2 | 2/2008 | Gordon et al. | |
| 7,331,996 | B2 | 2/2008 | Soto et al. | |
| 7,431,735 | B2 | 10/2008 | Liu et al. | |
| 7,445,636 | B2 | 11/2008 | Michelson | |
| 7,479,160 | B2 | 1/2009 | Branch et al. | |
| 7,500,992 | B2 | 3/2009 | Li | |
| 7,537,612 | B2 | 5/2009 | Kunzler | |
| 7,578,849 | B2 | 8/2009 | Trieu | |
| 7,584,682 | B2 * | 9/2009 | Hsiao | 74/425 |
| 7,608,107 | B2 | 10/2009 | Michelson | |
| 7,621,956 | B2 | 11/2009 | Paul et al. | |
| 7,674,296 | B2 | 3/2010 | Rhoda et al. | |
| 7,678,148 | B2 | 3/2010 | Peterman | |
| 7,682,376 | B2 | 3/2010 | Trieu | |
| 7,691,147 | B2 * | 4/2010 | Gutlin et al. | 623/17.15 |
| 7,703,727 | B2 | 4/2010 | Selness | |
| 7,727,280 | B2 * | 6/2010 | McLuen | 623/17.16 |
| 7,749,252 | B2 | 7/2010 | Zucherman et al. | |
| 7,753,958 | B2 * | 7/2010 | Gordon et al. | 623/17.15 |
| 7,758,617 | B2 | 7/2010 | Lott et al. | |
| 7,794,501 | B2 * | 9/2010 | Edie et al. | 623/17.12 |
| 7,799,081 | B2 | 9/2010 | McKinley | |
| D626,233 | S | 10/2010 | Cipoletti et al. | |
| 7,811,287 | B2 | 10/2010 | Errico et al. | |
| 7,811,327 | B2 | 10/2010 | Hansell et al. | |
| 7,828,849 | B2 | 11/2010 | Lim | |
| 7,837,688 | B2 | 11/2010 | Boyer, II et al. | |
| 7,837,734 | B2 | 11/2010 | Zucherman et al. | |
| 7,850,733 | B2 | 12/2010 | Baynham et al. | |
| 7,931,688 | B2 | 4/2011 | Landry et al. | |
| 7,932,825 | B2 | 4/2011 | Berger | |
| RE42,480 | E | 6/2011 | Bryan et al. | |
| 7,985,231 | B2 | 7/2011 | Sankaran | |
| 8,002,834 | B2 | 8/2011 | de Villiers et al. | |
| 8,062,375 | B2 | 11/2011 | Glerum et al. | |
| 8,070,813 | B2 | 12/2011 | Grotz et al. | |

(56) References Cited

U.S. PATENT DOCUMENTS

| | | | |
|---|---|---|---|
| 8,105,382 B2 | 1/2012 | Olmos et al. | |
| 8,110,004 B2 | 2/2012 | Valdevit et al. | |
| 8,187,332 B2 | 5/2012 | McLuen | |
| 8,221,502 B2 | 7/2012 | Branch, Jr. | |
| 8,262,666 B2 | 9/2012 | Baynham et al. | |
| 8,262,736 B2 | 9/2012 | Michelson | |
| 8,273,129 B2 | 9/2012 | Baynham et al. | |
| 8,282,683 B2 * | 10/2012 | McLaughlin et al. | 623/17.11 |
| 8,292,963 B2 * | 10/2012 | Miller et al. | 623/17.16 |
| 8,303,601 B2 | 11/2012 | Bandeira et al. | |
| 8,303,658 B2 | 11/2012 | Peterman | |
| 8,308,801 B2 | 11/2012 | Halverson et al. | |
| 8,308,804 B2 | 11/2012 | Krueger | |
| 8,317,025 B1 | 11/2012 | Kolozs et al. | |
| 8,328,962 B2 | 12/2012 | Schussler | |
| 8,337,562 B2 | 12/2012 | Landry et al. | |
| 8,343,222 B2 | 1/2013 | Cope | |
| 8,361,152 B2 | 1/2013 | McCormack et al. | |
| 8,366,777 B2 | 2/2013 | Matthis et al. | |
| 8,403,990 B2 | 3/2013 | Dryer et al. | |
| 8,444,696 B2 | 5/2013 | Michelson | |
| 8,444,697 B1 | 5/2013 | Butler et al. | |
| 8,585,763 B2 * | 11/2013 | Olevsky et al. | 623/17.16 |
| 8,591,587 B2 * | 11/2013 | Refai et al. | 623/17.15 |
| 8,597,360 B2 | 12/2013 | McLuen et al. | |
| 8,690,886 B2 * | 4/2014 | Fedorov et al. | 606/99 |
| 8,740,980 B2 * | 6/2014 | Merves | 623/17.15 |
| 8,894,710 B2 * | 11/2014 | Simpson et al. | 623/17.15 |
| 2002/0128716 A1 * | 9/2002 | Cohen et al. | 623/17.15 |
| 2002/0165613 A1 | 11/2002 | Lin et al. | |
| 2004/0024461 A1 | 2/2004 | Ferree | |
| 2004/0039448 A1 | 2/2004 | Pisharodi | |
| 2004/0087947 A1 | 5/2004 | Lim et al. | |
| 2004/0106998 A1 | 6/2004 | Ferree | |
| 2004/0127993 A1 | 7/2004 | Kast et al. | |
| 2004/0138750 A1 | 7/2004 | Mitchell | |
| 2004/0181285 A1 | 9/2004 | Simonson | |
| 2004/0204762 A1 | 10/2004 | Ralph et al. | |
| 2004/0230309 A1 | 11/2004 | DiMauro et al. | |
| 2004/0243238 A1 | 12/2004 | Arnin et al. | |
| 2005/0015149 A1 | 1/2005 | Michelson | |
| 2005/0038515 A1 | 2/2005 | Kunzler | |
| 2005/0065610 A1 | 3/2005 | Pisharodi | |
| 2005/0107878 A1 | 5/2005 | Conchy | |
| 2005/0278036 A1 | 12/2005 | Leonard et al. | |
| 2005/0283236 A1 | 12/2005 | Razian | |
| 2006/0052872 A1 | 3/2006 | Studer et al. | |
| 2006/0069436 A1 | 3/2006 | Sutton et al. | |
| 2006/0095136 A1 | 5/2006 | McLuen | |
| 2006/0116769 A1 | 6/2006 | Marnay et al. | |
| 2006/0122701 A1 | 6/2006 | Kiester | |
| 2006/0129244 A1 | 6/2006 | Ensign | |
| 2006/0149381 A1 | 7/2006 | Kim | |
| 2006/0190084 A1 | 8/2006 | Doubler et al. | |
| 2006/0200243 A1 | 9/2006 | Rothman et al. | |
| 2006/0241643 A1 | 10/2006 | Lim et al. | |
| 2006/0241764 A1 | 10/2006 | Michelson | |
| 2006/0241766 A1 | 10/2006 | Felton et al. | |
| 2006/0241767 A1 | 10/2006 | Doty | |
| 2006/0241770 A1 * | 10/2006 | Rhoda et al. | 623/17.15 |
| 2006/0241774 A1 | 10/2006 | Attali et al. | |
| 2006/0253201 A1 | 11/2006 | McLuen | |
| 2006/0276899 A1 | 12/2006 | Zipnick et al. | |
| 2006/0293752 A1 | 12/2006 | Moumene et al. | |
| 2006/0293753 A1 | 12/2006 | Thramann | |
| 2007/0050030 A1 | 3/2007 | Kim | |
| 2007/0067038 A1 | 3/2007 | Studer et al. | |
| 2007/0093897 A1 | 4/2007 | Gerbec et al. | |
| 2007/0093901 A1 * | 4/2007 | Grotz et al. | 623/17.11 |
| 2007/0191954 A1 * | 8/2007 | Hansell et al. | 623/17.15 |
| 2007/0233254 A1 * | 10/2007 | Grotz et al. | 623/17.11 |
| 2007/0255407 A1 * | 11/2007 | Castleman et al. | 623/17.11 |
| 2007/0255413 A1 * | 11/2007 | Edie | A61F 2/44 623/17.16 |
| 2007/0255415 A1 * | 11/2007 | Edie et al. | 623/17.16 |
| 2007/0270954 A1 | 11/2007 | Wu | |
| 2007/0270968 A1 | 11/2007 | Baynham et al. | |
| 2008/0009880 A1 | 1/2008 | Warnick et al. | |
| 2008/0015701 A1 | 1/2008 | Garcia et al. | |
| 2008/0021559 A1 | 1/2008 | Thramann | |
| 2008/0046083 A1 | 2/2008 | Hewko | |
| 2008/0051902 A1 | 2/2008 | Dwyer | |
| 2008/0077153 A1 | 3/2008 | Pernsteiner et al. | |
| 2008/0125778 A1 | 5/2008 | Li | |
| 2008/0132949 A1 | 6/2008 | Aferzon et al. | |
| 2008/0140207 A1 | 6/2008 | Olmos et al. | |
| 2008/0147193 A1 * | 6/2008 | Matthis et al. | 623/17.16 |
| 2008/0154381 A1 | 6/2008 | Parrish | |
| 2008/0208264 A1 | 8/2008 | Lazarof | |
| 2008/0269905 A1 | 10/2008 | Link | |
| 2008/0288076 A1 | 11/2008 | Soo et al. | |
| 2009/0099601 A1 | 4/2009 | Aferzon et al. | |
| 2009/0164020 A1 | 6/2009 | Janowski et al. | |
| 2009/0198241 A1 | 8/2009 | Phan | |
| 2009/0198245 A1 | 8/2009 | Phan | |
| 2009/0198338 A1 | 8/2009 | Phan | |
| 2009/0210061 A1 * | 8/2009 | Sledge | 623/17.15 |
| 2009/0222100 A1 | 9/2009 | Cipoletti et al. | |
| 2009/0222101 A1 | 9/2009 | de Villiers et al. | |
| 2009/0292361 A1 | 11/2009 | Lopez | |
| 2009/0299478 A1 | 12/2009 | Carls et al. | |
| 2010/0023057 A1 | 1/2010 | Aeschlimann et al. | |
| 2010/0057204 A1 * | 3/2010 | Kadaba et al. | 623/17.12 |
| 2010/0145456 A1 * | 6/2010 | Simpson et al. | 623/17.16 |
| 2010/0204795 A1 | 8/2010 | Greenhalgh | |
| 2010/0211119 A1 | 8/2010 | Refai et al. | |
| 2010/0211176 A1 | 8/2010 | Greenhalgh | |
| 2010/0222884 A1 * | 9/2010 | Greenhalgh | 623/17.11 |
| 2010/0234956 A1 | 9/2010 | Attia et al. | |
| 2010/0241231 A1 | 9/2010 | Marino et al. | |
| 2010/0256768 A1 | 10/2010 | Lim et al. | |
| 2010/0262247 A1 * | 10/2010 | Arnin | 623/17.16 |
| 2010/0280622 A1 | 11/2010 | McKinley | |
| 2010/0286779 A1 | 11/2010 | Thibodeau | |
| 2010/0286780 A1 | 11/2010 | Dryer et al. | |
| 2010/0292796 A1 | 11/2010 | Greenhalgh et al. | |
| 2010/0298939 A1 | 11/2010 | Delfosse et al. | |
| 2010/0324606 A1 | 12/2010 | Moskowitz et al. | |
| 2011/0015747 A1 * | 1/2011 | McManus et al. | 623/17.16 |
| 2011/0035011 A1 | 2/2011 | Cain | |
| 2011/0054621 A1 | 3/2011 | Lim | |
| 2011/0077738 A1 | 3/2011 | Ciupik et al. | |
| 2011/0087329 A1 | 4/2011 | Poulos | |
| 2011/0112587 A1 | 5/2011 | Patel et al. | |
| 2011/0130835 A1 * | 6/2011 | Ashley et al. | 623/17.11 |
| 2011/0130838 A1 | 6/2011 | Morgenstern Lopez | |
| 2011/0138948 A1 * | 6/2011 | Jimenez et al. | 74/424.82 |
| 2011/0160861 A1 * | 6/2011 | Jimenez | F16H 25/2056 623/17.16 |
| 2011/0172716 A1 * | 7/2011 | Glerum | 606/279 |
| 2011/0172774 A1 | 7/2011 | Varela | |
| 2011/0213465 A1 | 9/2011 | Landry et al. | |
| 2011/0218627 A1 | 9/2011 | Rampersaud et al. | |
| 2011/0230970 A1 | 9/2011 | Lynn et al. | |
| 2011/0238184 A1 | 9/2011 | Zdeblick et al. | |
| 2011/0282453 A1 | 11/2011 | Greenhalgh et al. | |
| 2011/0301712 A1 | 12/2011 | Palmatier et al. | |
| 2011/0319997 A1 | 12/2011 | Glerum et al. | |
| 2012/0035729 A1 | 2/2012 | Glerum et al. | |
| 2012/0058451 A1 | 3/2012 | Lazarof | |
| 2012/0059470 A1 | 3/2012 | Weiman | |
| 2012/0059472 A1 | 3/2012 | Weiman | |
| 2012/0059473 A1 | 3/2012 | Weiman | |
| 2012/0059474 A1 | 3/2012 | Weiman | |
| 2012/0059475 A1 | 3/2012 | Weiman | |
| 2012/0059481 A1 | 3/2012 | Abernathie et al. | |
| 2012/0064487 A1 | 3/2012 | Lazarof | |
| 2012/0064488 A1 | 3/2012 | Lazarof | |
| 2012/0071979 A1 | 3/2012 | Zipnick | |
| 2012/0089228 A1 | 4/2012 | Poulos | |
| 2012/0130494 A1 | 5/2012 | DeLurio et al. | |
| 2012/0136448 A1 | 5/2012 | Seifert et al. | |
| 2012/0143194 A1 | 6/2012 | Seifert et al. | |
| 2012/0143201 A1 | 6/2012 | Seifert et al. | |

(56) References Cited

U.S. PATENT DOCUMENTS

| | | |
|---|---|---|
| 2012/0150304 A1 | 6/2012 | Glerum et al. |
| 2012/0150305 A1 | 6/2012 | Glerum et al. |
| 2012/0158071 A1* | 6/2012 | Jimenez et al. ............ 606/86 A |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0191194 A1 | 7/2012 | Olmos et al. |
| 2012/0197404 A1 | 8/2012 | Brun et al. |
| 2012/0203347 A1 | 8/2012 | Glerum et al. |
| 2012/0209384 A1* | 8/2012 | Arnold et al. ............. 623/17.15 |
| 2012/0226357 A1 | 9/2012 | Varela |
| 2012/0232601 A1 | 9/2012 | Chabansky et al. |
| 2012/0245691 A1 | 9/2012 | Reimels |
| 2012/0271422 A1 | 10/2012 | Miller et al. |
| 2012/0277875 A1* | 11/2012 | Arnin ......................... 623/17.16 |
| 2012/0290090 A1 | 11/2012 | Glerum et al. |
| 2012/0303124 A1* | 11/2012 | McLuen et al. ........... 623/17.16 |
| 2012/0310350 A1* | 12/2012 | Farris et al. ............... 623/17.16 |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0006364 A1 | 1/2013 | McCormack et al. |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0023993 A1 | 1/2013 | Weiman |
| 2013/0023994 A1* | 1/2013 | Glerum ...................... 623/17.16 |
| 2013/0030534 A1 | 1/2013 | DeLurio et al. |
| 2013/0035724 A1 | 2/2013 | Fitzpatrick |
| 2013/0035763 A1 | 2/2013 | Krueger |
| 2013/0053962 A1 | 2/2013 | Moskowitz et al. |
| 2013/0085572 A1 | 4/2013 | Glerum et al. |
| 2013/0103153 A1 | 4/2013 | Blackwell et al. |
| 2013/0103156 A1* | 4/2013 | Packer et al. ............... 623/17.16 |
| 2013/0110248 A1 | 5/2013 | Zipnick |
| 2013/0158663 A1 | 6/2013 | Miller et al. |
| 2013/0158664 A1* | 6/2013 | Palmatier et al. .......... 623/17.16 |
| 2013/0158668 A1* | 6/2013 | Nichols et al. ............. 623/17.16 |
| 2013/0158669 A1* | 6/2013 | Sungarian et al. ......... 623/17.16 |
| 2013/0197642 A1* | 8/2013 | Ernst ..................... A61F 2/4465 623/17.16 |
| 2013/0204371 A1* | 8/2013 | McLuen et al. ........... 623/17.16 |
| 2013/0211525 A1* | 8/2013 | McLuen et al. ........... 623/17.16 |
| 2013/0253650 A1* | 9/2013 | Ashley et al. .............. 623/17.16 |
| 2013/0274883 A1* | 10/2013 | McLuen et al. ........... 623/17.16 |
| 2013/0310938 A1* | 11/2013 | Sournac et al. ............ 623/17.15 |
| 2014/0088708 A1* | 3/2014 | McLaughlin et al. ..... 623/17.15 |
| 2014/0156006 A1* | 6/2014 | Bannigan et al. .......... 623/17.15 |
| 2014/0236296 A1* | 8/2014 | Wagner et al. ............ 623/17.15 |
| 2014/0249629 A1* | 9/2014 | Moskowitz et al. ....... 623/17.15 |
| 2014/0257485 A1* | 9/2014 | Matthis et al. ............. 623/17.15 |
| 2014/0277470 A1* | 9/2014 | Baynham ................... 623/17.13 |
| 2014/0277500 A1* | 9/2014 | Logan et al. ............... 623/17.16 |
| 2014/0277509 A1* | 9/2014 | Robinson et al. .......... 623/17.16 |
| 2014/0288652 A1* | 9/2014 | Boehm et al. ............. 623/17.15 |
| 2014/0316522 A1* | 10/2014 | Weiman et al. ............ 623/17.16 |
| 2014/0343677 A1* | 11/2014 | Davis et al. ................ 623/17.15 |
| 2014/0343678 A1* | 11/2014 | Suddaby et al. ........... 623/17.16 |
| 2015/0094814 A1* | 4/2015 | Emerick et al. ............ 623/17.16 |

\* cited by examiner

BONE FUSION DEVICE

RELATED APPLICATIONS

This application claims priority under 35 U.S.C. §119(e) of U.S. Provisional Patent Application Ser. No. 61/624,155, filed Apr. 13, 2012, and entitled "BONE FUSION DEVICE," which is hereby incorporated by reference.

FIELD OF THE INVENTION

This invention relates generally to bone fusion devices. More specifically, the present invention relates to devices for fusing vertebrae of the spine that can be inserted arthroscopically.

BACKGROUND OF THE INVENTION

The spinal column is made up of vertebrae stacked on top of one another. Between the vertebrae are discs which are gel-like cushions that act as shock-absorbers and keep the spine flexible. Injury, disease, or excessive pressure on the discs can cause degenerative disc disease or other disorders where the disc becomes thinner and allows the vertebrae to move closer together or become misaligned. As a result, nerves may become pinched, causing pain that radiates into other parts of the body, or instability of the vertebrae may ensue.

One method for correcting disc-related disorders is to insert a fusion cage between the vertebrae to act as a structural replacement for the deteriorated disc. The fusion cage is typically a hollow metal device usually made of titanium. Once inserted, the fusion cage maintains the proper separation between the vertebrae to prevent nerves from being pinched and provides structural stability to the spine. Also, the inside of the cage is filled with bone graft material which eventually fuses permanently with the adjacent vertebrae into a single unit.

The use of fusion cages for fusion and stabilization of vertebrae in the spine is known in the prior art. U.S. Pat. No. 4,961,740 to Ray, et al. entitled, "V-Thread Fusion Cage and Method of Fusing a Bone Joint," discloses a fusion cage with a threaded outer surface, where the crown of the thread is sharp and cuts into the bone. Perforations are provided in valleys between adjacent turns of the thread. The cage can be screwed into a threaded bore provided in the bone structure at the surgical site and then packed with bone chips which promote fusion.

U.S. Pat. No. 5,015,247 to Michelson entitled, "Threaded Spinal Implant," discloses a fusion implant comprising a cylindrical member having a series of threads on the exterior of the cylindrical member for engaging the vertebrae to maintain the implant in place and a plurality of openings in the cylindrical surface.

U.S. Pat. No. 6,342,074 to Simpson entitled, "Anterior Lumbar Underbody Fusion Implant and Method For Fusing Adjacent Vertebrae," discloses a one-piece spinal fusion implant comprising a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopaedic screw to be retained entirely within the access passage.

U.S. Pat. No. 5,885,287 to Bagby entitled, "Self-tapping Interbody Bone Implant," discloses a bone joining implant with a rigid, implantable base body having an outer surface with at least one bone bed engaging portion configured for engaging between a pair of bone bodies to be joined, wherein at least one spline is provided by the bone bed engaging portion, the spline being constructed and arranged to extend outwardly of the body and having an undercut portion.

U.S. Pat. No. 6,582,467 to Teitelbaum et al. entitled, "Expandable Fusion Cage," discloses an expandable fusion cage where the surfaces of the cage have multiple portions cut out of the metal to form sharp barbs. As the cage is expanded, the sharp barbs protrude into the subcortical bone of the vertebrae to secure the cage in place. The cage is filled with bone or bone matrix material.

U.S. Pat. No. 5,800,550 to Sertich entitled, "Interbody Fusion Cage," discloses a prosthetic device which includes an inert generally rectangularly shaped support body adapted to be seated on hard end plates of vertebrae. The support body has top and bottom faces. A first peg is movably mounted in a first aperture located in the support body, and the first aperture terminates at one of the top and bottom faces of the support body. Further, the first peg projects away from the one of the top and bottom faces and into an adjacent vertebra to secure the support body in place relative to the vertebra.

U.S. Pat. No. 6,436,140 to Liu et al. entitled, "Expandable Interbody Fusion Cage and Method for Insertion," discloses an expandable hollow interbody fusion device, wherein the body is divided into a number of branches connected to one another at a fixed end and separated at an expandable end. The expandable cage may be inserted in its substantially cylindrical form and may be expanded by movement of an expansion member to establish lordosis of the spine. An expansion member interacts with the interior surfaces of the device to maintain the cage in the expanded condition and provide a large internal chamber for receiving bone in-growth material.

These patents all disclose fusion cage devices that can be inserted between vertebrae of the spine in an invasive surgical procedure. Such an invasive surgical procedure requires a long recovery period.

SUMMARY OF THE INVENTION

The present invention is directed to a bone fusion device for insertion between bones that are to be fused together, such as, for example, the vertebrae of a spinal column. The bone fusion device comprises at least one extendable tab and one or more tab extension assemblies. Each tab extension assembly is able to be adjusted in order to individually control the extension or contraction of a side of the tab thereby enabling adjustment of the height and/or angle of the tab with respect to the body of the bone fusion device. The bone fusion device is in its most compact state when the tab is aligned with the body of the device such that the tab lies within the exterior of the body of the device. In this compact form, the bone fusion device is preferably inserted between the vertebrae by using an arthroscopic procedure. After the device has been positioned between the vertebrae, the tab is extended using the extension assemblies such that the tab abuts the bottom surface of the upper vertebrae. The angle of the tab with respect to the body of the device is able to be adjusted such that it corresponds to the vertebrae. Specifically, each extension assembly is able to be individually adjusted such that the side controlled by each assembly is raised or lowered until the desired tab angle is achieved. In this way, the tab is advantageously positioned and angled to correspond to the vertebrae to help brace the device until the bone has fused and to provide a larger surface area to which the bones attach and fuse during a healing period.

A first aspect of the present application is directed to a bone fusion device for insertion into a desired location. The device comprises a body having an interior cavity, a tab configured to fit within the interior cavity and selectively move from a retracted position within interior cavity of the body to an extended position extending out of the body and a plurality of extension assemblies coupled to a different portion of the tab and configured to move the different portions of the tab between the retracted position and the extended position independent of the remainder of the extension assemblies. In some embodiments, each of the extension assemblies comprise a worm gear operably coupled between a drive screw and a support jack such that rotation of the drive screw rotates the worm gear which retracts or extends the support jack into or out of the worm gear. In some embodiments, at least one of the drive screws of the extension assemblies is accessible through a first lateral side of the body and at least a second one of the drive screws is accessible through a second lateral side of the body. In some embodiments, the extension assemblies are pivotably coupled to the different portions of the tab such that the tab is able to pivot about the extension assembly. In some embodiments, the body has a bottom surface and an upper surface, wherein the upper surface is angled with respect to the bottom surface. In some embodiments, the device further comprises one or more plugs, wherein the body and the tab comprise one or more holes that extend from outside the device to the inner cavity and are configured to be removably filled by the plugs. In some embodiments, the plugs comprise bone material. In some embodiments, the tab comprises one or more tangs positioned along the perimeter of the top surface of the tab and fit within recesses in the top surface of the body when the tab is in the retracted position. In some embodiments, one or more of the tangs extend from the perimeter of the tab to the perimeter of the body. In some embodiments, the device further comprises a support webbing positioned within the inner cavity of the body between one or more walls of the inner cavity and the exterior of the worm gears such that the support webbing resists lateral movement of the worm gears with respect to the walls of the inner cavity.

A second aspect of the present application is directed to a method of implanting a bone fusion device into a desired location. The method comprises inserting the bone fusion device in the desired location, wherein the bone fusion device comprises a body having an interior cavity, a tab configured to fit within the interior cavity and selectively move from a retracted position within interior cavity of the body to an extended position extending out of the body and a plurality of extension assemblies coupled to a different portion of the tab and configured to move the different portions of the tab between the retracted position and the extended position independent of the remainder of the extension assemblies and independently extending one or more of the different portions of the tab from the retracted position within the interior cavity to a position at least partially outside the interior cavity by moving at least one of the extension assemblies. In some embodiments, the method further comprises adjusting the amount which one or more of the different portions of the tab are extended compared to the remainder of the different portions of the tab such that the angle of the tab with respect to the body is adjusted. In some embodiments, each of the extension assemblies comprise a worm gear operably coupled between a drive screw and a support jack such that rotation of the drive screw rotates the worm gear which retracts or extends the support jack into or out of the worm gear. In some embodiments, at least one of the drive screws of the extension assemblies is accessible through a first lateral side of the body and at least a second one of the drive screws is accessible through a second lateral side of the body. In some embodiments, the extension assemblies are pivotably coupled to the different portions of the tab such that the tab is able to pivot about the extension assembly. In some embodiments, the body has a bottom surface and an upper surface, wherein the upper surface is angled with respect to the bottom surface. In some embodiments, the method further comprises removably filling one or more holes with one or more plugs, wherein the body and the tab comprise the one or more holes, which extend from outside the device to the inner cavity and are configured to be removably filled by the plugs. In some embodiments, the plugs comprise bone material. In some embodiments, the tab comprises one or more tangs positioned along the perimeter of the top surface of the tab and fit within recesses in the top surface of the body when the tab is in the retracted position. In some embodiments, one or more of the tangs extend from the perimeter of the tab to the perimeter of the body. In some embodiments, the device further comprises a support webbing positioned within the inner cavity of the body between one or more walls of the inner cavity and the exterior of the worm gears such that the support webbing resists lateral movement of the worm gears with respect to the walls of the inner cavity. In some embodiments, the method further comprises retracting the tab of the bone fusion device into the retracted position before inserting the bone fusion device into the desired location.

A third aspect of the present application is directed to a distraction instrument for use with a bone fusion device. The distraction instrument comprises a tubular body, a control rod positioned at least partially within the tubular body, wherein the control rod comprises a first end coupled with a handle and extending out a first side of the tubular body and a second end including an engaging element and extending out a second side of the tubular body and a head assembly comprising a plurality of plates and operably coupled with engaging element of the control rod such that manipulating the control rod with respect to the head assembly causes the plates to separate. In some embodiments, the head assembly is operably coupled with the engaging element such that rotation of the control rod with respect to the head assembly causes the plates to separate and rotation in the opposite direction causes the plates to contract. In some embodiments, the head assembly further comprises a jack mechanism coupled between the plates that effectuates the separating and the contracting of the plates and is configured to fit within one or more recesses within the plates when the plates are fully contracted. In some embodiments, the instrument further comprises an indicator positioned on the surface of the instrument, wherein the indicator dynamically indicates the distance between the plates. In some embodiments, the indicator indicates one or more values corresponding to how much one or more controls of one or more bone fusion implant devices must be rotated to extend one or more tabs of the devices such that the devices have height equal to the distance between the plates. In some embodiments, the instrument further comprises a force sensor coupled to the head assembly, wherein the force sensor measures a level of force resisting the separation of the plates. In some embodiments, the indicator indicates the level of force measured by the force sensor. In some embodiments, the head assembly is configured to stop the plates from further separating once the level of force measured by the force sensor equals a threshold level. In some embodiments, the instrument further comprises a motor and a motor control coupled with the control rod, wherein the motor control controls the operation of the motor and the motor enables motorized manipulation of the control rod to separate the plates.

A fourth aspect of the present application is directed to a method of using a distraction instrument to measure the amount of space in a desired location. The method comprises inserting the distraction instrument in the desired location, wherein the distraction instrument comprises a tubular body, a control rod positioned at least partially within the tubular body, wherein the control rod comprises a first end coupled with a handle and extending out a first side of the tubular body and a second end including an engaging element and extending out a second side of the tubular body and a head assembly comprising a plurality of plates and operably coupled with engaging element of the control rod such that moving the control rod with respect to the head assembly causes the plates to separate and separating the plates until the plates reach bounds of the desired location by manipulating the control rod with respect to the head assembly. In some embodiments, the manipulating the control rod comprises rotating the control rod with respect to the head assembly wherein rotation in a first direction causes the plates to separate and rotation in a second direction causes the plates to contract. In some embodiments, the head assembly further comprises a jack mechanism coupled between the plates that effectuates the separating and the contracting of the plates and is configured to fit within one or more recesses within the plates when the plates are fully contracted. In some embodiments, the instrument further comprises an indicator positioned on the surface of the instrument, wherein the indicator dynamically indicates the distance between the plates. In some embodiments, the indicator indicates one or more values corresponding to how much one or more controls of one or more bone fusion implant devices must be rotated to extend one or more tabs of the devices such that the devices have height equal to the distance between the plates. In some embodiments, the instrument further comprises a force sensor coupled to the head assembly, wherein the force sensor measures a level of force resisting the separation of the plates. In some embodiments, the indicator indicates the level of force measured by the force sensor. In some embodiments, the head assembly is configured to stop the plates from further separating once the level of force measured by the force sensor equals a threshold level. In some embodiments, the instrument further comprises a motor and a motor control coupled with the control rod, wherein the motor control controls the operation of the motor and the motor enables motorized manipulation of the control rod to separate the plates.

A fifth aspect of the present application is directed to a bone fusion device for insertion into a desired location. The device comprises a body having an interior cavity, a tab configured to fit within the interior cavity and selectively move from a retracted position within interior cavity of the body to an extended position extending out of the body, a plurality of extension assemblies coupled to a different portion of the tab and configured to move the tab between the retracted position and the extended position and a position locking mechanism operably coupled with each of the plurality of extension assemblies and configured to provide a plurality of locking positions that the plurality of extension assemblies are biased to stay in by the position locking mechanism. In some embodiments, the plurality of extension assemblies are configured to move the different portions of the tab between the retracted position and the extended position independent of the remainder of the extension assemblies. In some embodiments, the position locking mechanism comprises a dial operably coupled with one of the plurality of extension assemblies such that when the one of the plurality of extension assemblies is rotated the dial is also rotated. In some embodiments, the position locking mechanism comprises one or more stops operably coupled with the dial such that when the one of the plurality of extension assemblies is in one of the locking positions the interface between the dial and the stops provides a biasing force that resists the movement of the one of the plurality of extension assemblies out of the one of the locking positions.

DETAILED DESCRIPTION

In the following description, numerous details and alternatives are set forth for purpose of explanation. However, one of ordinary skill in the art will realize that the invention can be practiced without the use of these specific details. For instance, the figures and description below often refer to the vertebral bones of a spinal column. However, one of ordinary skill in the art will recognize that some embodiments of the invention are practiced for the fusion of other bones, including broken bones and/or joints. In other instances, well-known structures and devices are shown in block diagram form in order not to obscure the description of the invention with unnecessary detail. Further, although the figures and description below refer to a bone fusion device having a single tab and a pair of tab extension assemblies, it is understood that the bone fusion device is able to comprise multiple tabs each having any number of tab extension assemblies.

Figure 1A:
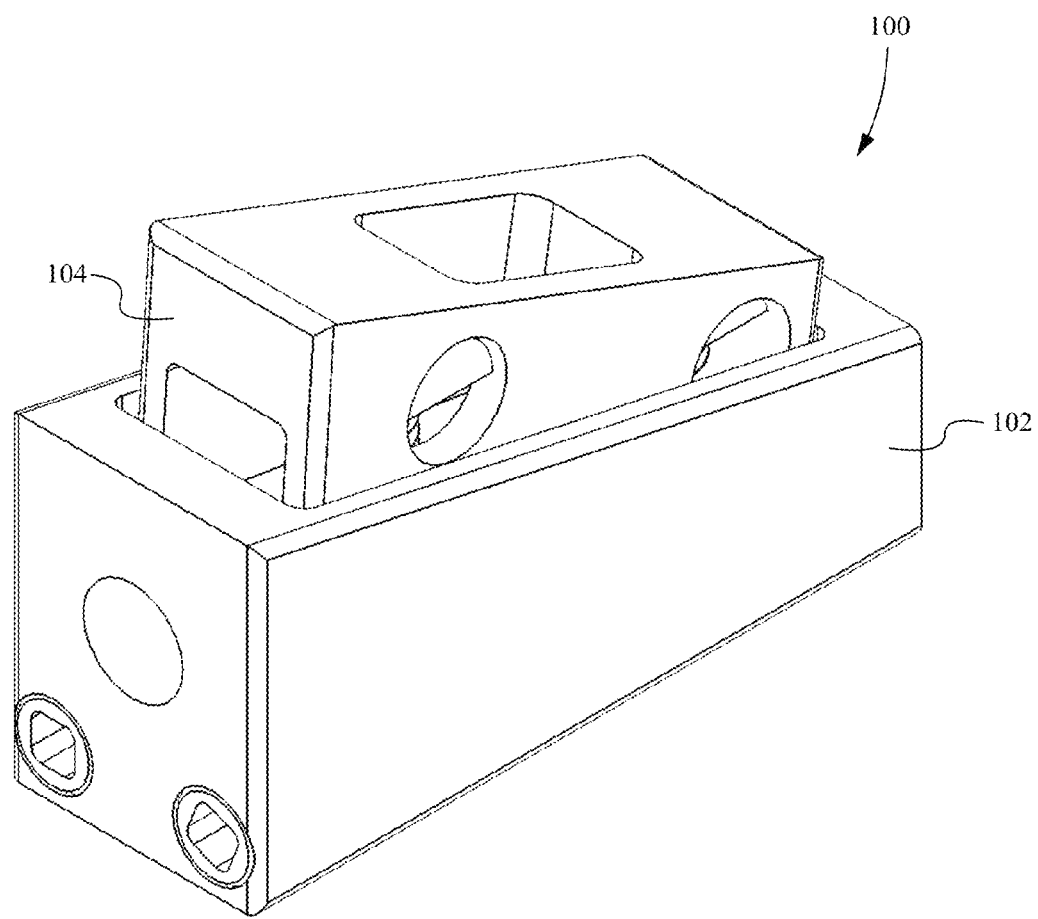
FIG. 1A illustrates an external perspective view of a bone fusion device according to some embodiments.
Figure 1B:
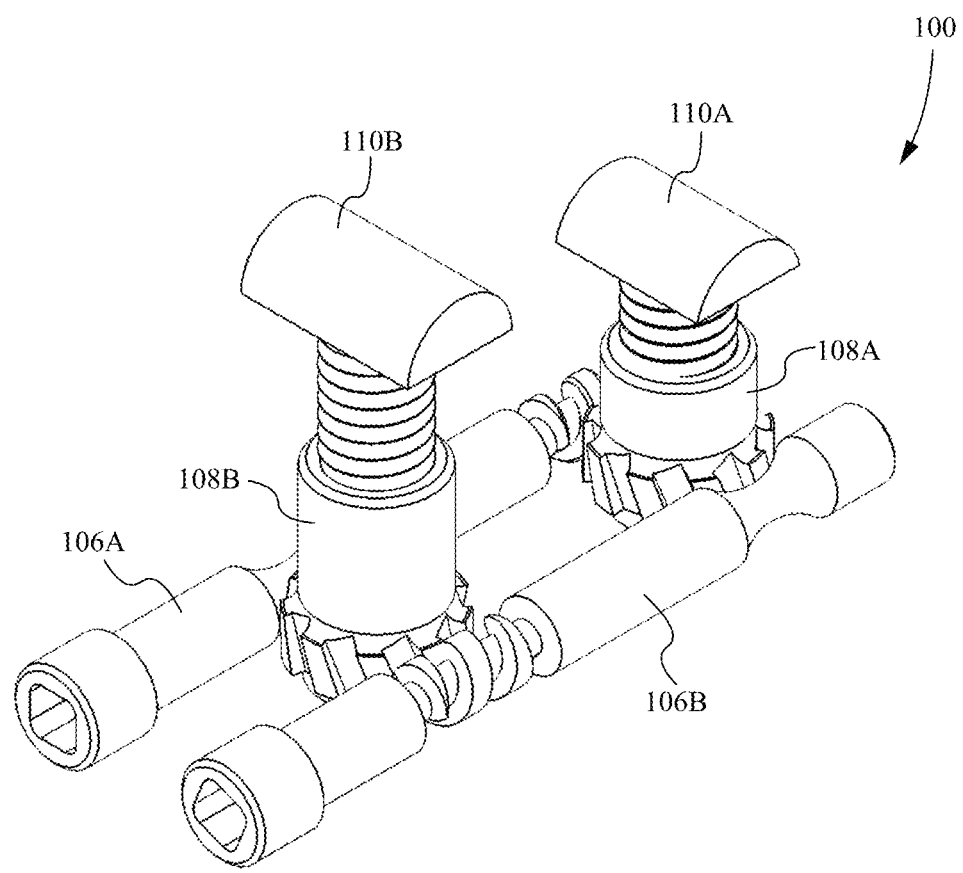
FIG. 1B illustrates an internal perspective view of a bone fusion device according to some embodiments.

FIGS. 1A and 1B illustrate an external and internal perspective view of a bone fusion device 100 according to some embodiments. As shown in FIGS. 1A and 1B, the bone fusion device 100 comprises a body 102, at least one tab 104 and a plurality of tab extension assemblies each comprising a drive screw 106A, 106B, a gear 108A, 108B and a supporting jack 110A, 110B. Alternatively, the device 100 is able to comprise a single tab extension assembly. The front tab extension assembly comprises a front drive screw 106A which is mechanically coupled to a front supporting jack 110A via a front gear 108A, and the back tab extension assembly comprises a rear drive screw 106B which is mechanically coupled to a rear supporting jack 110B via a rear gear 108B. As a result, the supporting jacks 110A, 110B are able to be individually and selectively raised or lowered with respect to the gears 108A, 108B by rotating or otherwise manipulating the corresponding drive screws 106A, 106B of the extension assemblies. As shown in FIG. 1A, when combined with the body 102 and tab 104, the drive screws 106A, 106B are able to be positioned within a pair of screw channels 204 of the body 102 (see FIG. 2) and the supporting jacks 110A, 110B are able to couple with the jack holes 208 at the front and rear of the tab 104. Accordingly, by accessing and adjusting the drive screws 106A, 106B of the tab extension assemblies through the screw channels 204 of the body 102, a user is able to not only selectively extend and retract the tab 104 a desired distance from the body 102, but also is able to adjust the angle of the tab 104 by lowering or raising the sides of the tab 104 with respect to each other. Alternatively, the tab extension assemblies are able to comprise other components for selectively raising or lowering the tab 104 such as a plurality of angled extending blocks that are able to be individually controlled by drive screws such that they press against the tab 104 to selectively extend/retract and adjust the angle of the tab 104.

The bone fusion device 100 is able to be constructed from a high strength biocompatible material, such as titanium, which has the strength to withstand forces in the spine that are generated by a patient's body weight and daily movements. Alternatively, part or all of the bone fusion device 100 is able to be constructed from one or more of the group consisting of ceramics, high strength biocompatible material, a polymer such as PEEK, PEKK and other polymeric materials, stainless steel, titanium, titanium alloys such as nitinol and other biocompatible metals. In some embodiments, the materials used to construct the bone fusion device include using additives, such as carbon fibers for better performance of the materials under various circumstances. The base biocompatible material is often textured or coated with a porous material conducive to the growth of new bone cells on the bone fusion device 100.

It should be noted that although FIGS. 1A and 1B illustrate a single tab 104 having a pair of extension assemblies, the bone fusion device 100 is able to comprise any number of tabs 104 each having any number of extension assemblies. Further, although the extension assemblies are shown as coupling to a front end and a back end of the tab 104, the assemblies are able to be coupled to any portion of the tab 104 such that the angle of the tab 104 in any plane is able to be adjusted using the extension assemblies. In particular, for each tab extension assembly coupled to a tab 104, another side or portion of the tab 104 is able to be selectively raised or lowered with respect to the body 102 and/or other portions of the tab 104.

Figure 2:
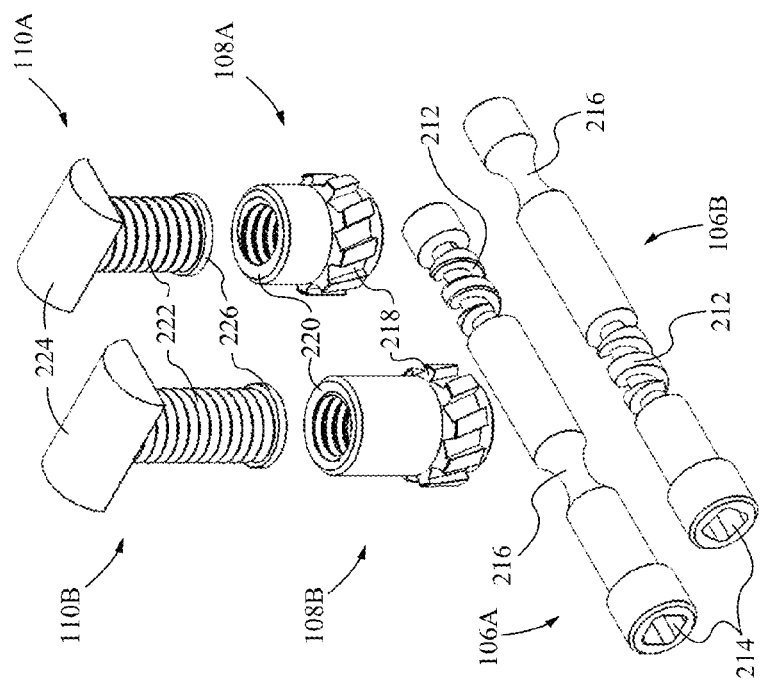
FIG. 2 illustrates a perspective view of the components of the bone fusion device according to some embodiments.
Figure 2:
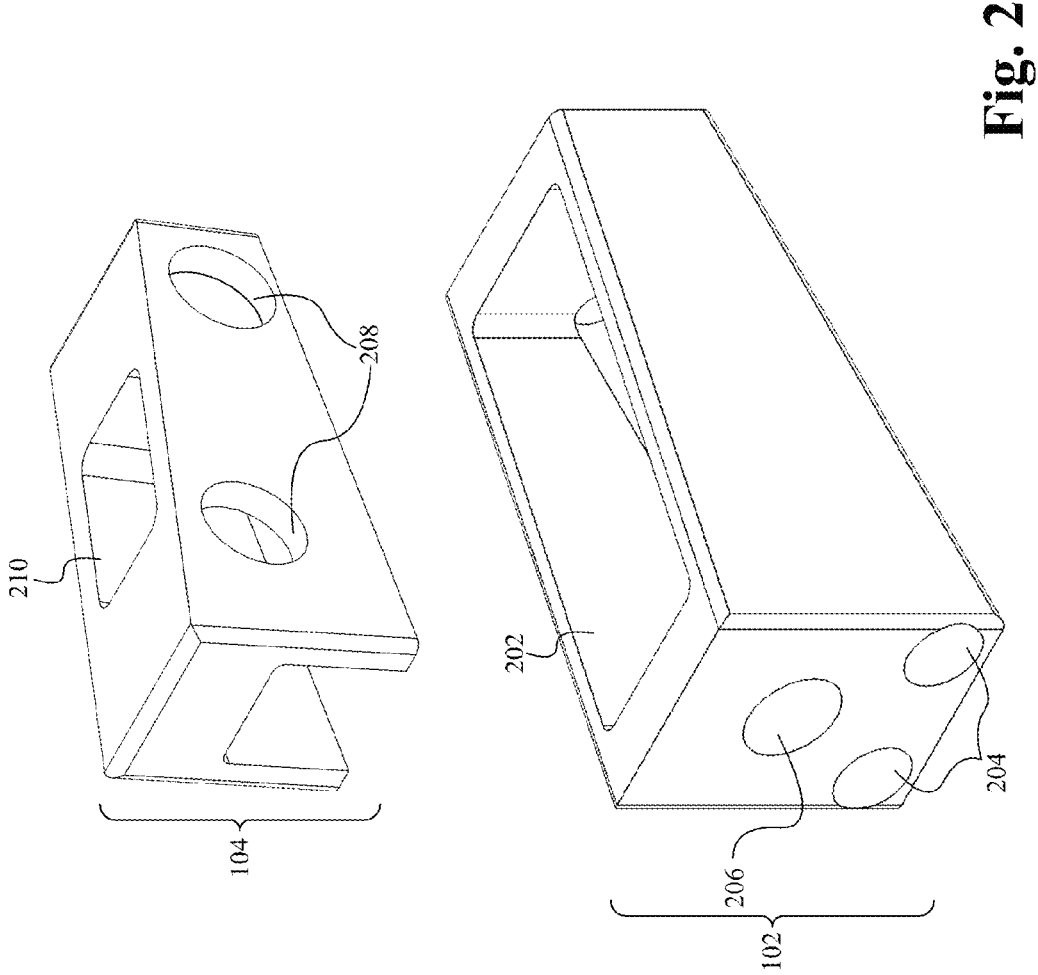

FIG. 2 illustrates a perspective view of the components of the bone fusion device 100 according to some embodiments. As shown in FIG. 2, the body 102 comprises a body cavity 202 for housing the other components in a retracted state, one or more screw channels 204 for receiving the drive screws 106A, 106B, and one or more body apertures 206 for providing access to the cavity 202. Specifically, the body 102 houses the tab 104 and tab extension assemblies within the body cavity 202 such that when the device 100 is in a retracted state the tab 104 and tab extension assemblies are all positioned within the outer dimensions of the body 102. This enables the bone fusion device 100 to have the smallest profile possible when in the tab 104 is retracted thereby minimizing the size of the required surgical incision for the bone fusion surgery.

In some embodiments, the body 102 has a substantially rectangular structure with an angled upper surface that aligns with the upper surface of the tab 104 when the tab 104 is retracted. In some embodiments, the upper surface of the body 102 is angled downward from front to back such that the front wall is higher than the back wall. Alternatively, the upper surface of the body 102 is able to be angled upward from front to back and/or otherwise angled. Alternatively, the body 102 is able to comprise other shapes such as shapes that substantially conform to the shape of vertebrae. In some embodiments, the screw channels 204 positioned such that the screws 106A, 106B are accessible from the same side of the body 102. Alternatively, the channels 204 are able to be positioned such that the screws 106A, 106B are accessible from one or more different sides of the body 102. The apertures 206 of the body 102 extend from the cavity 202 to the exterior of the body 102. As a result, the apertures 206 permit bone graft material to be inserted into the device 100 and to contact the vertebral bone before or after the device 100 has been inserted between the vertebrae of the patient. As used herein, bone graft material is able to refer to materials, biologics or other structures that promote osteoinduction and/or osteoconduction as are well known in the art. For example, the bone graft material is able to comprise, in combination or separately, one or more of autologous bone, allograft bone, artificial bone paste, artificial bone putty, osteoinduction material, osteoconduction material or other "scaffolding" for bone to grow upon and to induce bone growth as are well known in the art. The bone graft material and the surface texturing of the device 100 encourage the growth and fusion of bone from the neighboring vertebrae. The fusion and healing process will result in the bone fusion device 100 aiding in the bridging of the bone between the two adjacent vertebral bodies of the spine which eventually fuse together during the healing period. Additionally, it is understood that although as shown in FIG. 2, the body 102 comprises a single aperture 206 positioned on a rear surface, the body 102 is able to comprise any number of apertures 206 positioned on any of the surfaces of the body 102.

In some embodiments, the body 102 of the bone fusion device 100 comprises one or more gripping channels (not shown) each having at least one gripping aperture. In such embodiments, the gripping apertures are able to receive the gripping fingers of a bone fusion device insertion instrument such that the instrument cannot slip out of place during operation. In particular, the gripping channels and insertion instrument are able to be substantially similar in operation and structure to the bone fusion device channels and bone fusion device insertion instrument described in U.S. Provisional Application No. 61/521,681, filed Aug. 9, 2011 and entitled "BONE FUSION DEVICE, APPARATUS AND METHOD," which is hereby incorporated by reference. As a result, an insertion instrument is able to grip and insert the bone fusion device 100 while preventing or at least minimizing the risk of the insertion instrument and/or bond fusion device 100 slipping out of place. Indeed, this security is necessary to ensure that the surgeon is able to precisely place and control the device 100 within a patient during surgery.

As shown in FIG. 2, the tab 104 comprises one or more tab apertures 210 and one or more jack holes 208 such that there is at least one jack hole 208 for each jack 110A, 110B. Specifically, the jack holes 208 are positioned and sized such that the ends of the jack heads 224 of the jacks 110A, 110B are able to couple to the tab 104 by being positioned within the jack holes 208. For example, in some embodiments a pair of jack holes 208 are able to be positioned across from each other on the tab 104 such that the holes 208 straddle each jack head 224 preventing the jack 110A, 110B from separating from the tab 104. In some embodiments, the jack holes 208 (and at least a portion of the profile of the jack heads 224) are substantially circular such that when coupled to the jacks 110A, 110B, the jacks 110A, 110B are able to rotate within the jack holes 208 with respect to the tab 104. In particular, this rotational coupling provides the advantage of enabling the angle of tab 104 with respect to the body 102 and/or extension assemblies to be adjusted because the rotation of the jacks 110A, 110B within the holes 208 corresponds to the angle change of the tab 104 with respect to the body 102 and/or assemblies. Alternatively, the jack holes 208 and jack heads 224 are able to comprise ball joints or other shapes and/or profiles that enable both coupling and rotation as are well known in the art.

Figure 21A:
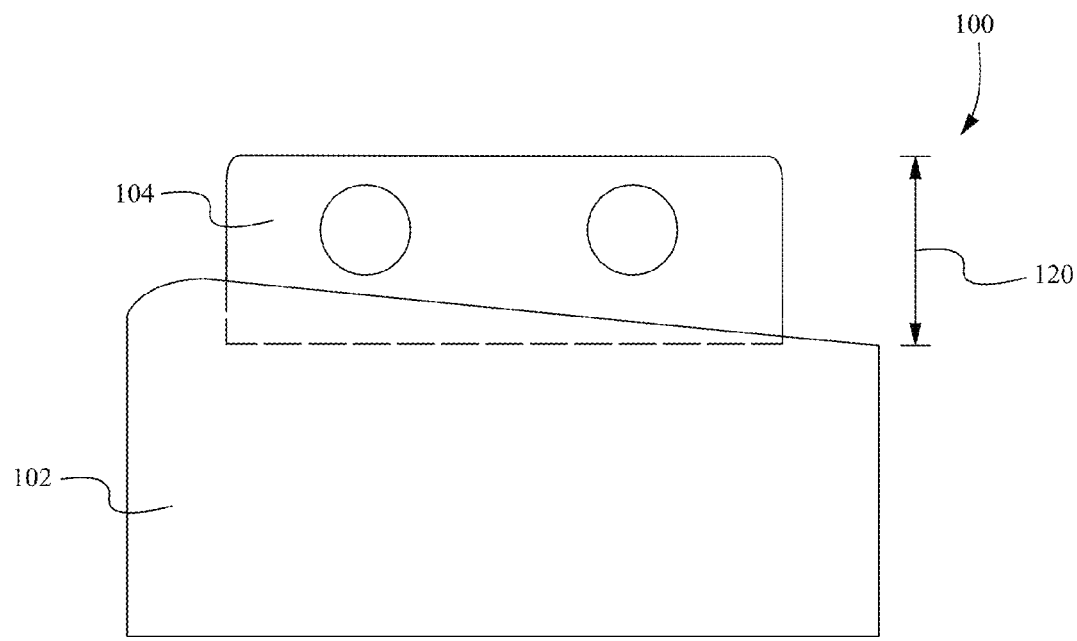
FIG. 21A illustrates a bone fusion device with a tab configured to have the maximum parallel distraction according to some embodiments.
Figure 21B:
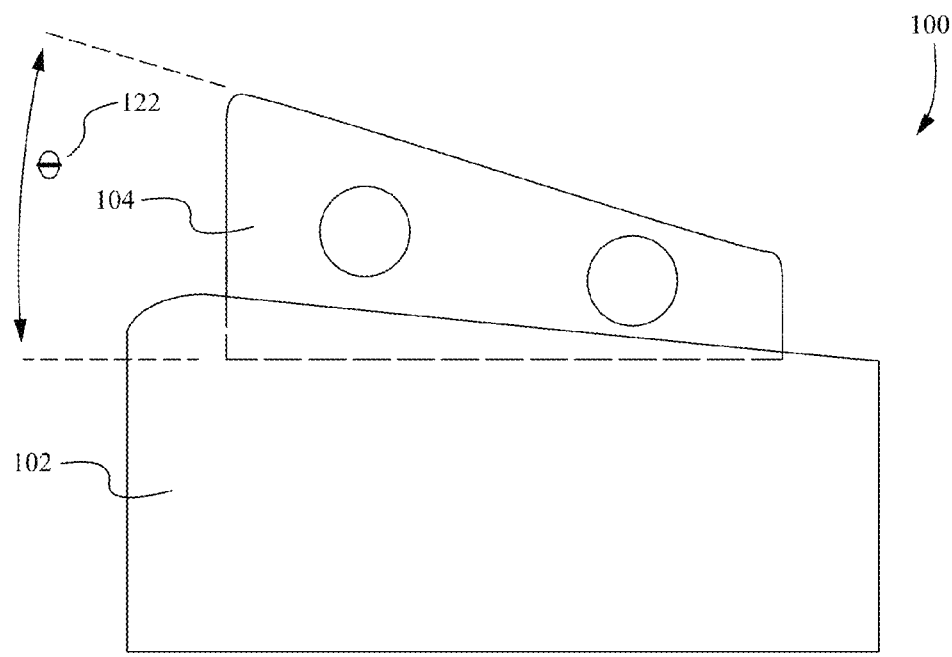
FIG. 21B illustrates a bone fusion device with a tab configured to have the maximum angle according to some embodiments.

The tab 104 is shaped such that the tab 104 is able to fit within the cavity 202 of the body 102. For example, in some embodiments the tab 104 is shaped such that its perimeter profile matches the perimeter of the cavity 202 and/or such that the outwardly facing surface of the tab 104 is substantially flush with the frame 114 of the bone fusion device 100 when the tab 104 is in the retracted position. In some embodiments, the upper surface of the tab 104 is angled downward from front to back such that the front wall is higher than the back wall. Alternatively, the upper surface of the tab 104 is able to be angled upward from front to back and/or otherwise angled. Alternatively, the tab 104 is able to comprise other shapes as are well known in the art. In some embodiments, tabs 104 having upper surfaces of varying angles are able to be interchanged within the bone fusion device 100. As a result, a user is able to exchange the current tab 104 of a device 100 with a different tab 104 having a differently angled upper surface. This allows the same bone fusion device 100 to be switched from having the maximum parallel distraction 120 with a tab 104 with a parallel upper surface as shown in FIG. 21A to the maximum angle 122 with a tab 104 having the maximum angled upper surface as shown in FIG. 21B or angles in between. In some embodiments, the outwardly facing surface of the tab 104 has sharp serrated edges, protrusions, ridges or threads along the length of the tab 104 for engaging the adjacent vertebrae. Further, it is understood that although as shown in FIG. 2, the tab 104 comprises a single tab aperture 210 positioned on an upper surface, the tab 104 is able to comprise any number of tab apertures 210 positioned on any of the surfaces of the tab 104.

As shown in FIG. 2, the drive screws 106A, 106B each comprise a positioning aperture 214, a threaded portion 212 and a recessed portion 216, the gears 108A, 108B each comprise gear teeth 218 and interior threading 220, and the jacks 110A, 110B each comprise a jack head 224, exterior threading 222 and a bottom protrusion 226. Specifically, as shown in FIG. 1B, the threaded portion 212 of the drive screws 106A, 106B is positioned such that the threads align with the gear teeth 218 of one of the gears 108A, 108B and the interior threading 220 of the gears 108A, 108B matches the exterior threading 222 of the jack heads 224 when the jack heads 224 are positioned within the gears 108A, 108B. As a result, when the drive screws 106A, 106B are rotated, the threaded portion 212 applies force to the gear teeth 218 rotating the interior threading 220 of the gears 108A, 108B. This rotation causes the interior threading to apply force to the exterior threading 222 of the jacks 110A, 110B causing the jacks 110A, 110B to extend out of or retract further within the gears 108A, 108B. In particular, if the screws 106A, 106B are rotated in a first direction, the jacks 110A, 110B are extended out of the gears 108A, 108B until the bottom protrusion 226 reaches the interior threading 220 (see FIG. 3B). Conversely, if the screws 106A, 106B are rotated in an opposite second direction, the jacks 110A, 110B are retracted further within the gears 108A, 108B until the bottom of the jack heads 224 abut the upper surface of the gears 108A, 108B (see FIG. 3A). Thus, when coupled to the tab 104, by rotating the drive screws 106A, 106B, the tab extension assemblies are able to selectively retract/extend and adjust the angle of the tab 104 with respect to the body 102. Alternatively, one or more of the drive screws 106A, 106B, gears 108A, 108B and/or jacks 110A, 110B are able to be mechanically coupled using other mechanically coupling components as are well known in the art. For example, a universal joint is able to be used instead of the threaded portion 212 and gear teeth 218 in order to translate the rotation of the drive screws 106A, 106B to the gears 108A 108B.

The positioning apertures 214 of the drive screws 106A, 106B are positioned on the end of the screws 106A, 106B such that they are accessible when the drive screws 106A, 106B are within the screw channels 204 of the body 102. As a result, a user is able to insert one or more tool engaging members (not shown) into the positioning apertures 214 in order to rotate the drive screws 106A, 106B. The structure of the positioning apertures 214 is configured such that the structure enables one or more engaging members of tools to rotate the drive screws 106A, 106B. For example, the positioning apertures 214 are able to match the engaging members of allen wrenches, flat-head screw drivers, phillips screw drivers and/or the engaging members of other types of tools as are well known in the art. The recessed portions 216 of the drive screws 106A, 106B are positioned such that they are adjacent to and/or surround the gear 108A, 108B that is not mechanically coupled to the threaded portion 212 of that drive screw 106A, 106B. As a result, the recessed portions 216 are able to help hold the gears 108A, 108B and screws 106A, 106B in place with respect to each other while not translating the rotation of the screws 106A, 106B to the gear 108A, 108B of the other tab extension assembly. Alternatively, the recessed portions 216 are able to be omitted. For example, the recessed portions 216 are able to be omitted and the threaded portion 212 is able to protrude out from the cylindrical body of the screws 106A, 106B in order to maintain mechanical coupling with the gear teeth 218. In some embodiment, the body 102 further comprises one or more tool channels (not shown) that selectively couple with a tool when the engaging member of the tool is coupled with one or more of the positioning apertures 214. As a result, the tool and its engaging member is able to be prevented from slipping out of the positioning apertures 214 which is able to cause harm to a patient during an insertion procedure.

Figure 3A:
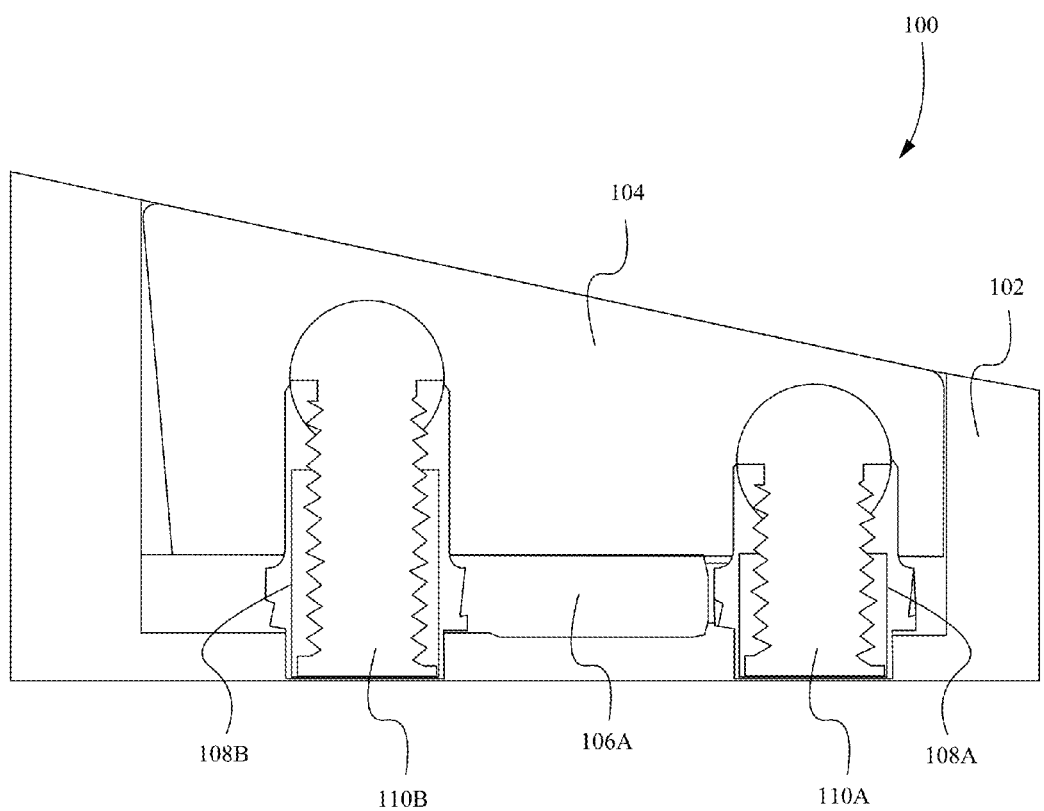
FIG. 3A illustrates a cross sectional view of the bone fusion device with the tab retracted according to some embodiments.
Figure 3B:
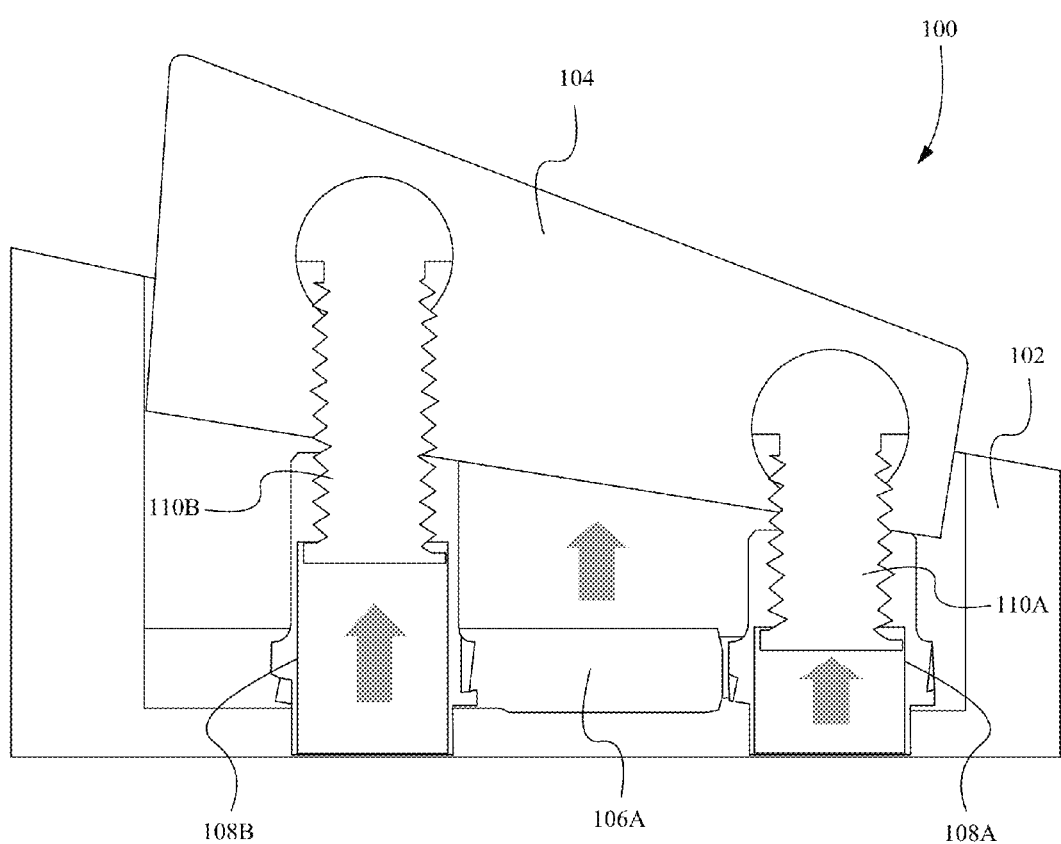
FIG. 3B illustrates a cross sectional view of the bone fusion device with the tab extended according to some embodiments.

FIGS. 3A and 3B illustrate cross sectional view of the bone fusion device 100 with the tab 104 fully retracted and fully extended, respectively, according to some embodiments. As shown in FIG. 3A, when the device is in the retracted position, the jacks 110A, 110B are fully retracted within the gears 108A, 108B and the outward facing surface of the tab 106 is substantially flush with the upper surface of the body 102. While in this position, the bone fusion device 100 creates the smallest profile possible and thus is able to be surgically inserted between two vertebrae of a patient with a minimally invasive procedure. As shown in FIG. 3B, once in position, the surgeon is able to use one or more tools (not shown) to rotate the drive screws 106A, 106B of the tab extension assemblies until the tab 104 has been raised to a desired height by the jacks 110A, 110B. Further, the surgeon is able to individually raise or lower the jacks 110A, 110B such that the tab 104 is rotated and the upper angle of the tab 104 with respect to the body 102 is adjusted. Accordingly, the bone fusion device 100 provides the advantage of enabling not only the tab height to be adjusted to a desired level, but also that the tab angle to be adjusted to a desired degree in order to best correspond to the vertebrae thereby increasing the stability of the bone fusion and the success of the surgery.

Figure 5:
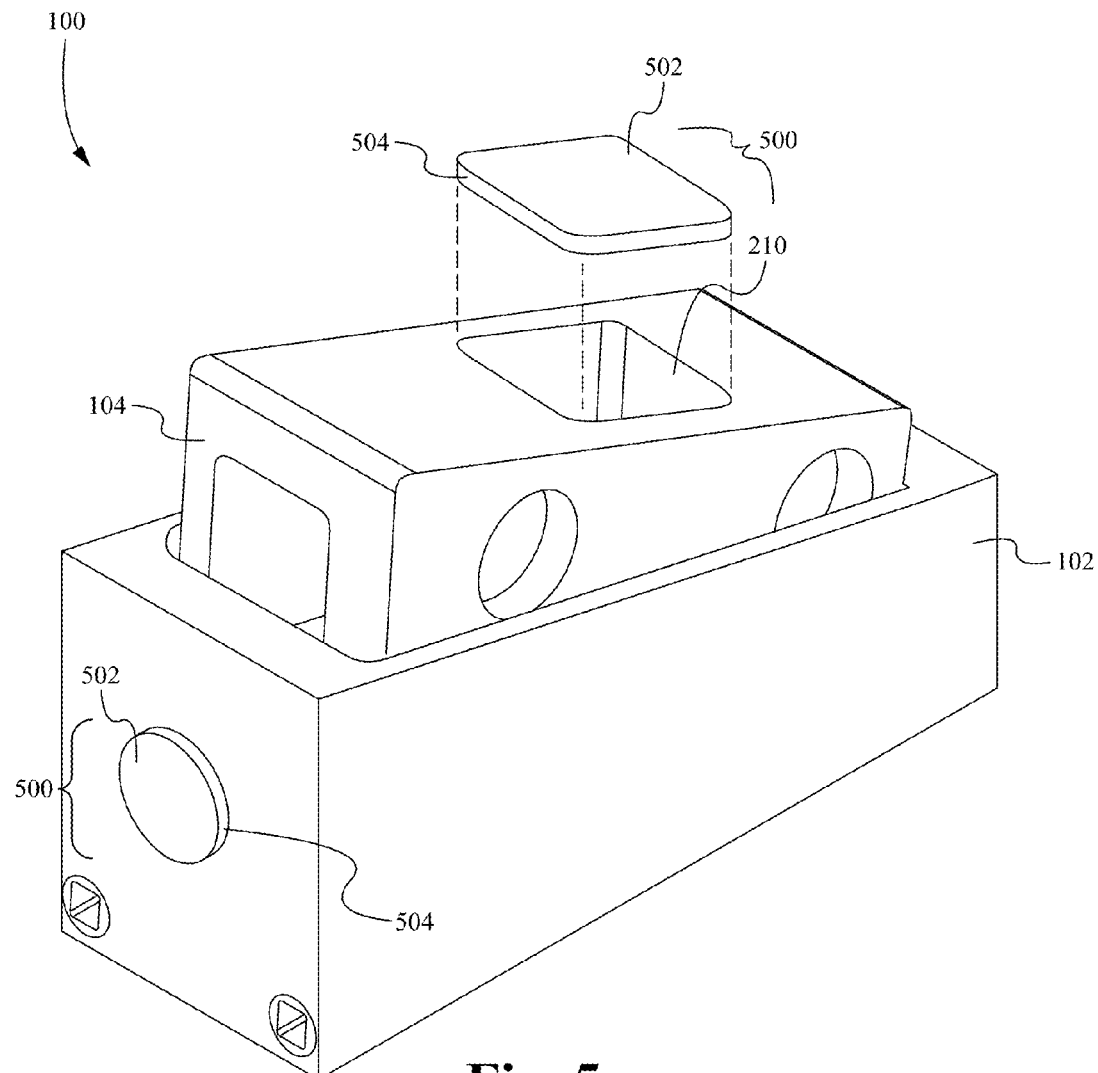
FIG. 5 illustrates the bone fusion device comprising one or more bone plugs according to some embodiments.

FIG. 5 illustrates the bone fusion device 100 comprising one or more bone plugs 500 according to some embodiments. As shown in FIG. 5, the bone plugs 500 comprise a plug body 502 having at least one desired profile or perimeter 504. Specifically, the perimeter 504 of the plug body 502 is sized such that the plug 500 fits within one or more of the tab 104 or body 102 apertures 210, 206. As a result, one or more bone plugs 500 are able to be used to fill one or more of the apertures of the bone fusion device 100. This creates the benefit of reducing the amount of bone graft material that needs to be inserted into the cavity 202 of the bone fusion device 100. In some embodiments, the bone fusion device 100 comprises at least one bone plug 500 for each aperture within the body 102 and/or the tab 104. Alternatively, at least one of the apertures within the body 102 and/or the tab 104 are able to remain "unplugged" such that bone graft material is able to be injected into the device 100 through the unplugged apertures. In some embodiments, the bone plugs 500 are sized such that the perimeter 504 will contact the inner surface of the apertures 210, 206 when the bone plug 500 is inserted into the aperture such that friction from the contact will hold the plug 500 in place. In some embodiments, the perimeter 504 is able to be sized slightly larger than the inner surface of the apertures 210, 206 such that upon insertion into an aperture either the aperture or the plug 500 flexes, wherein the resistance to the flexing provides a force holding the plug or plugs 500 in place within the aperture. Alternatively, the plugs 500 are able to have differently shaped perimeters 504 as are well known in the art.

In some embodiments, the body 502 of one or more of the plugs 500 has a thickness greater than the thickness of the apertures 206, 210 such that the plugs 500 are able to protrude into and/or out of the bone fusion device 100 when positioned within one of the apertures 206, 210. Alternatively, the body 502 is able to be less thick and/or be positioned such that body 502 aligns with the surface of the bone fusion device 100 when inserted in an aperture 206, 210. In some embodiments, the body 502 of the plugs 500 comprises bone. Alternatively, the body 502 is able to comprise one or more materials selected from the group consisting of bone, bone graft material capable of retaining a desired shape, bone-like substances known to aid in the fusion process and other biocompatible materials as are well known in the art. In some embodiments, the one or more of the plugs 500 are flexible. Alternatively, the plugs 500 are able to be inflexible or rigid. Although the bone plugs 500 are described in reference to the bone fusion device 100, it is understood that they are able to be sized in order to fill the apertures of other types of bone fusion devices.

Figure 4:
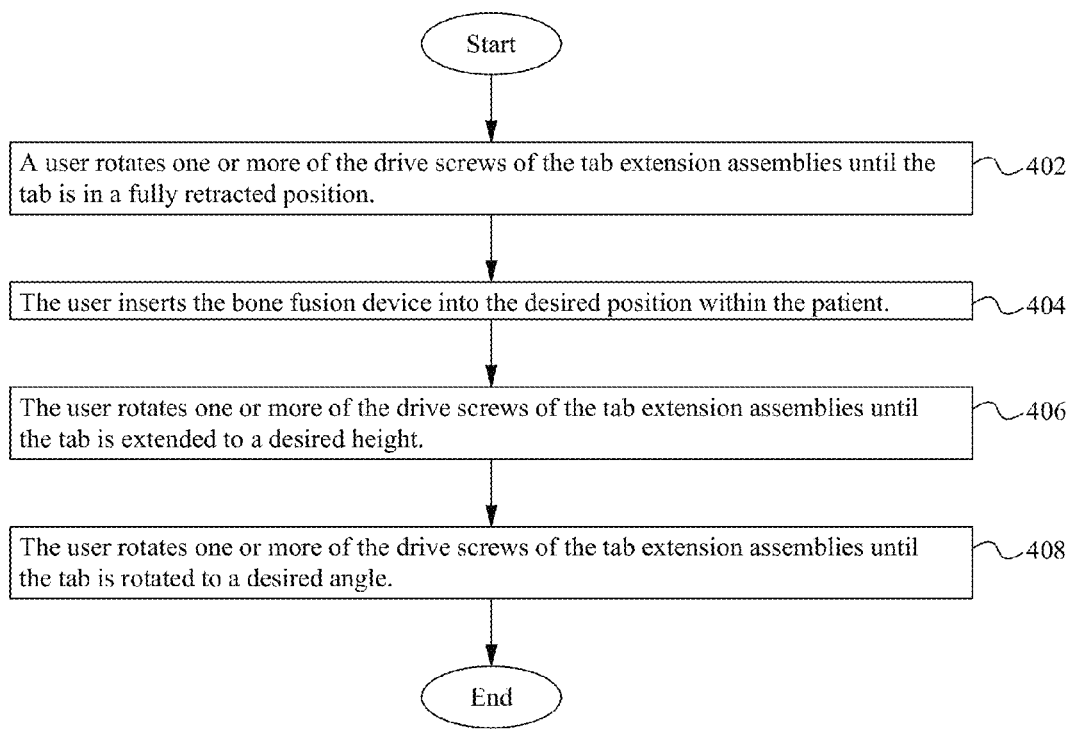
FIG. 4 illustrates a flow chart of a method of operating the bone fusion device according to some embodiments.

FIG. 4 illustrates a flow chart of a method of operating the bone fusion device 100 according to some embodiments. A user rotates one or more of the drive screws 106A, 106B of the tab extension assemblies until the tab 104 is in a fully retracted position at the step 402. The user inserts the bone fusion device 100 into the desired position within the patient at the step 404. In some embodiments, the desired position comprises between or adjacent to one or more vertebrae. In some embodiments, the bone fusion device 100 is inserted anteriorly. Alternatively, the bone fusion device 100 is able to be inserted posteriorly, laterally, far lateral, extra lateral, extreme lateral, transforaminaly, or other directions as are well known in the art. The user rotates one or more of the drive screws 106A, 106B of the tab extension assemblies until the tab 104 is extended to a desired height at the step 406. In some embodiments, the desired height comprises the height required such that the tab 104 abuts the vertebrae. The user rotates one or more of the drive screws 106A, 106B of the tab extension assemblies until the tab 104 is rotated to a desired angle at the step 408. In some embodiments, the device 100 comprises a single tab extension assembly such that only the drive screw or screws associated with the single tab extension assembly need to be rotated. In some embodiments, the desired angle comprises the angle required to cause the outward facing surface of the tab 104 to substantially match the angle of the surface of the adjacent vertebrae. In some embodiments, the angle of the surface of the tab 104 is able to be adjusted before and/or during the extension of the tab 104 to the desired height. As a result, the tab 104 and the remainder of the bone fusion device 100 is able to exert a satisfactory force between the bone fusion device and the bones to be fused. At that point the bone fusion device 100 is able to remain in place. Thereafter, in some embodiments, material, such as autograft material, for fusing the bones together is able to be inserted through the apertures 206, 210 of the bone fusion device 100 to promote healing. Alternatively, the insertion of the material is able to be omitted or occur before insertion of the bone fusion device 100. In some embodiments, the method is able to comprise a plurality of bone fusion devices 100 that are each able to be used as described herein. In such embodiments, the plurality of bone fusion devices 100 are able to be inserted and/or adjusted together or separately. Alternatively, a single bone fusion device 100 is able to be used. For example, a single bone fusion device 100 is able to be used for a cervical surgery operation. Therefore, the bone fusion device 100 provides the advantage of a small incision and minimally invasive (arthroscopic) surgical procedure which advantageously promotes health and rapid recovery by the patient. Preferably, bone growth occurs around the bone fusion device and particularly at the location of the extended tab, such that the bone fusion device is further secured by the bone growth, which further promotes a superior, robust bone fusion result.

Figure 6A:
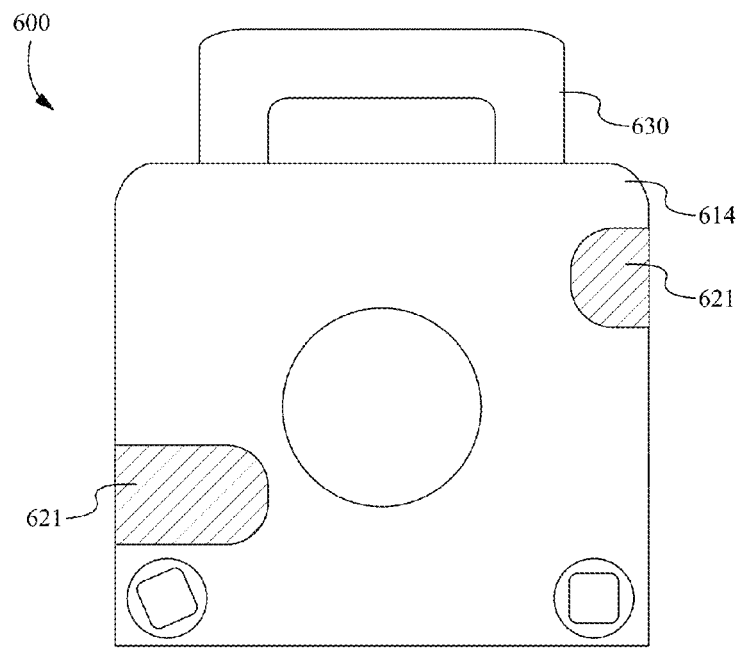
FIG. 6A illustrates a frontal view of a bone fusion device according to some embodiments.
Figure 6B:
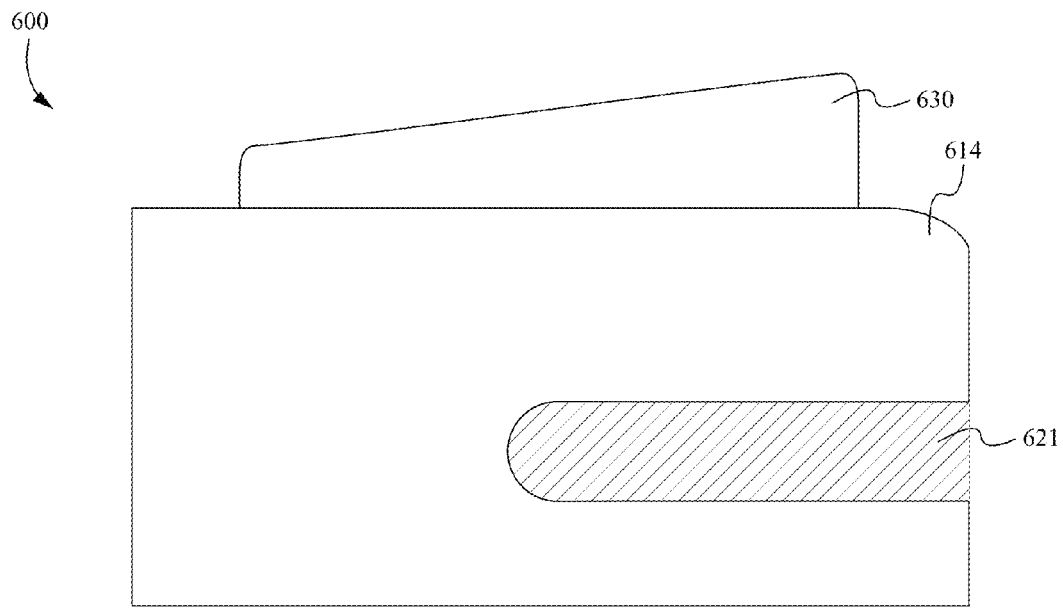
FIG. 6B illustrates a side view of a bone fusion device according to some embodiments.
Figure 6C:
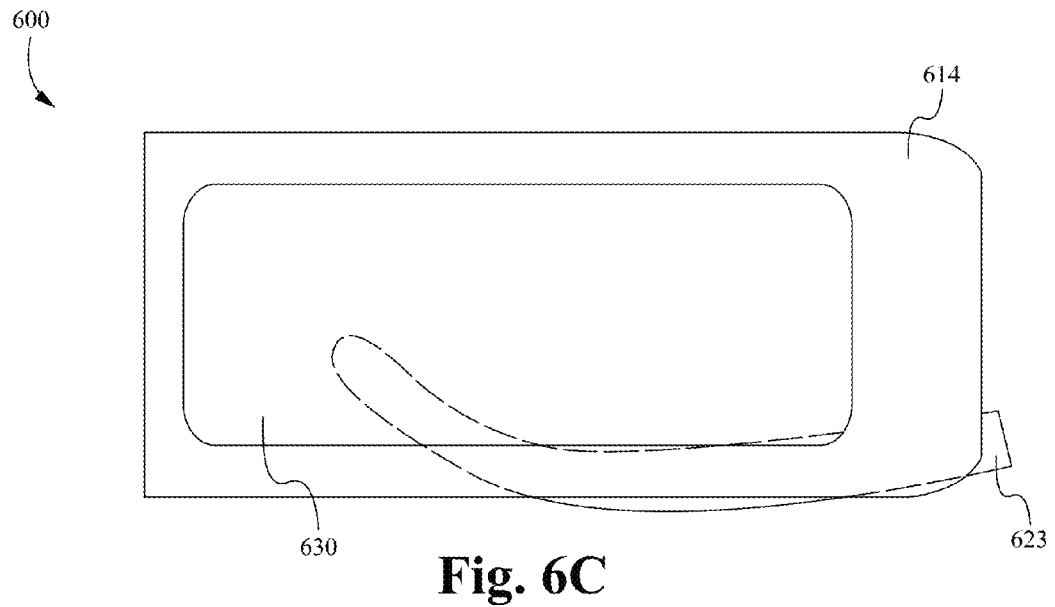
FIG. 6C illustrates a top view of an elongated member inserted within a canal of a bone fusion device according to some embodiments.

FIGS. 6A-C illustrate a front, side and top view of a bone fusion device 600 having one or more canals 621 according to some embodiments. The bone fusion device 600 shown in FIGS. 6A-C is substantially similar to the bone fusion device 100 except for the differences described herein. In particular, the bone fusion device 600 comprises a body 614 having one or more canals 621 and one or more tabs 630. In some embodiments, the canals 621 are positioned along the sides of the body 614 and a sized such that the canals 621 are able to receive or house a portion or all of one or more elongated members 623 (see FIG. 6D). Alternatively, one or more of the canals 621 are able to be positioned within other portions of the body 614 including different angles and orientations in one or all axises of the bone fusion device 600. Alternatively, one or more of the canals 621 are able to be positioned within one or more of the tabs 630. In some embodiments, the canals 621 extend from a central area of the body 614 to the front or back side of the body 614 such that an elongated member 623 is able to enter the canals 621 from the front or back side of the body 614 (and/or the side of the body 614). Alternatively, one or more of the canals 621 extend along the entire bone fusion device 600 from the front side to the back side of the body 614 (or vice versa), such that an elongated member 623 is able to enter the canals 621 from both or either the front or back side of the body 614. Alternatively, one or more of the canals 621 are able to be housed entirely within an inner portion of the body 614 such that the canals 621 breach neither the front nor the back side of the body 614 and the elongated members 623 are only able to enter the canals 621 from the side of the body 614.

FIG. 6C illustrates a top view of an elongated member 623 inserted within a canal 621 of the bone fusion device 600 according to some embodiments. As shown in FIG. 6C, the elongated member 623 is curved and extends from the front of the body 614 and canal 621 to a central portion of the body 614. Alternatively, the elongated members 623 are able to be configured such that the members 623 extend to the front, back, or other portions of the body 614. In some embodiments, one or more of the elongated member 621 are able to extend out of the canals 621 into the central cavity of the body 614 and/or outside of the body 614. For example, the members 623 are able to be curved or otherwise shaped such that the members 623 enter a desired portion of the body 614 while not extending out of the side of the body 614 more than a desired distance (e.g. 1 mm). In some embodiments, the desired portion of the body 614 in which the members 623 are positioned comprise between the front or back side of the body 614. Alternatively, the members 623 are able to be configured such that the members 623 are able to remain entirely within the canals 621 and/or cavity of the body 614. Additionally, it should be noted that one or more of the components of the bone fusion device 600 is able to be incorporated into the other bone fusion devices described herein.

Figure 6D:
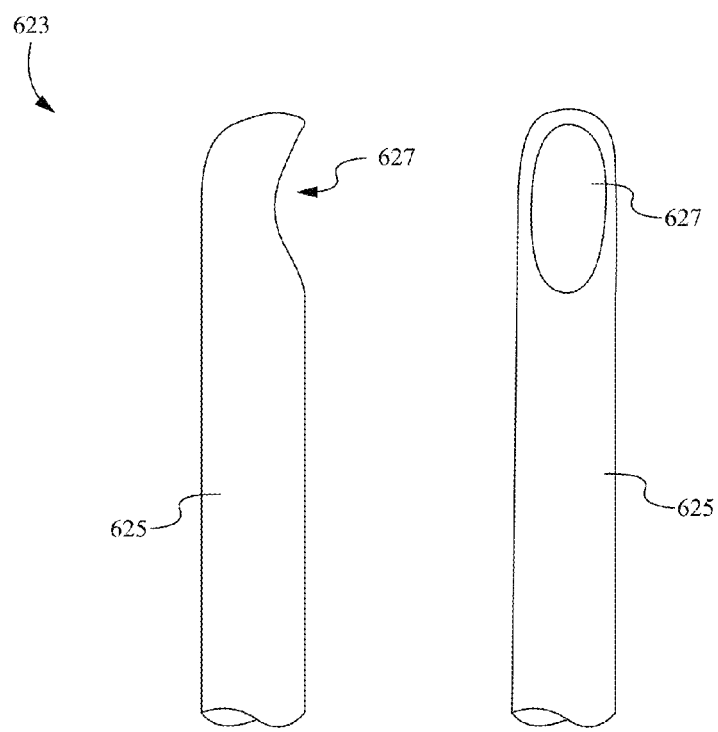
FIG. 6D illustrates a frontal and profile view of an elongated member according to some embodiments.

FIG. 6D illustrates a frontal and profile view of an elongated member 623 according to some embodiments. As shown in FIG. 6D, the elongated member 623 comprises a body 625 and one or more apertures 627. The body 625 is sized such that the member 623 is able to partially or wholly fit within the canals 621. In some embodiments, the body 625 is able to be tubular such that material, such as autograft material, is able to be inserted into the body 625 via the apertures 627. Alternatively, the body 625 is able to be partially or wholly solid, wherein if the body 625 is wholly solid the apertures 627 are able to be omitted. Alternatively, the body 625 is able to comprise other solid or hollow shapes as are well known in the art. As shown in FIG. 6D, the body 625 of the elongated member 623 is substantially straight. Alternatively, the body 625 is able to comprise one or more curves and/or corners as are well known in the art. For example, as shown in FIG. 6C, the body 625 is able to be curved such that the member 623 is able to curve from the canal 621 into the cavity of the body 614 of the bone fusion device 600. In some embodiments, the elongated member 623 is able to be bendable such that body 625 is able to be bended to a desired shape by a user and the body 625 will retain the desired shape. In some embodiments, the body 625 is filled with one or more of calcium triphosphate, hydroxyapatite or other materials that are constituents of bone or promote bone growth as are well known in the art. In some embodiments, the body 625 is able to comprise materials that are constituents of bone or promote bone growth as are well known in the art. Alternatively, the body 625 is able to comprise the same or similar materials to that of the bone fusion device 600. As a result, the bone fusion device 600 and the elongated members 623 are able to be used to position bone grafting promotive material along the device 600 after the bone fusion device 600 has been positioned into place within a patient. This enables the bone fusion device 600 to ensure that the bone fusion material is not pushed out of place during the extension of the tabs 630 or other portions of the procedure.

Figure 6E:
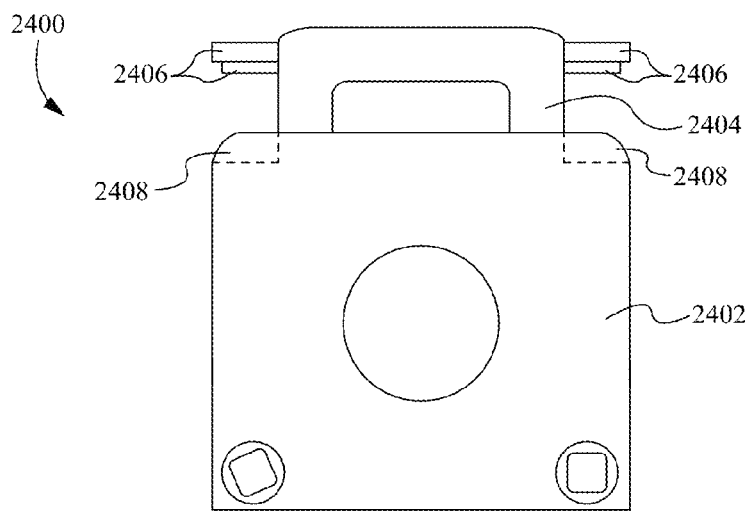
FIG. 6E illustrates a front view of the bone fusion device having one or more tangs according to some embodiments.
Figure 6F:
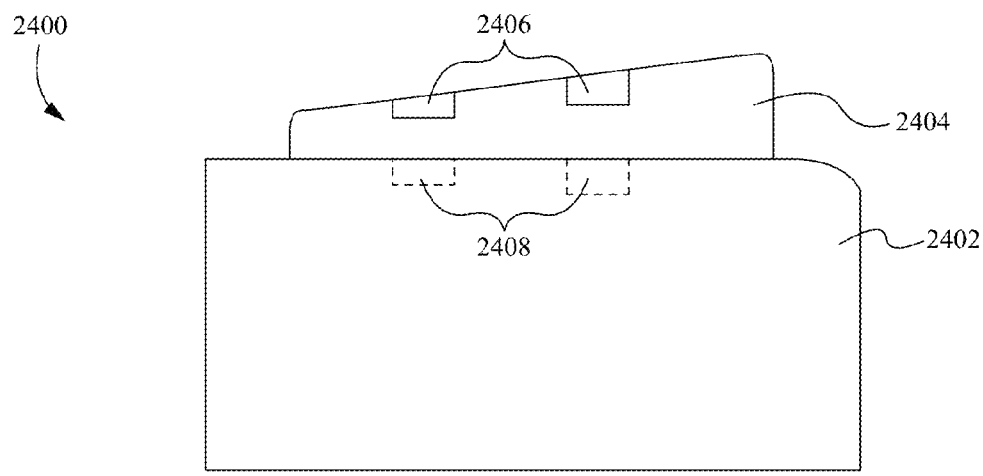
FIG. 6F illustrates a profile view of the bone fusion device having one or more tangs according to some embodiments.
Figure 6G:
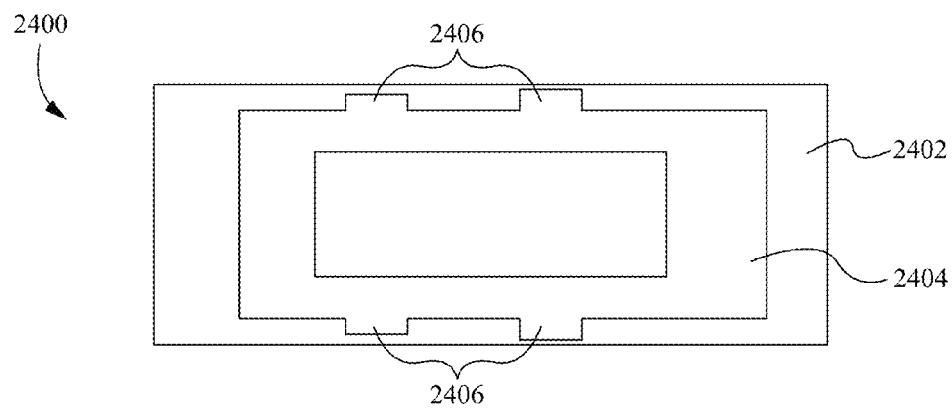
FIG. 6G illustrates a top view of the bone fusion device having one or more tangs according to some embodiments.

FIGS. 6E-G illustrate a front, profile and top view of the bone fusion device 2400 having one or more tangs 2406 according to some embodiments. The bone fusion device 2400 shown in FIGS. 6E-G is substantially similar to the bone fusion device 100 except for the differences described herein. In particular, the bone fusion device 2400 comprises a body 2402 having one or more tang recesses 2408 and one or more tabs 2404 having one or more tangs 2406. The tangs 2406 extend from one or more of the tabs 2404 and increase the surface area of the tabs 2404 thereby promoting bone growth and aiding the fusion process. The tang recesses 2408 are sized and positioned to receive or house each of the tangs 2406 when the tabs 2404 are retracted into the body 2402 in order to maintain the minimal size of the device 2400 when in the retracted position. In some embodiments, each tang 2406 has a separate corresponding tang recess 2408. Alternatively, one or more of the tang recesses 2408 are able to house a plurality of tangs 2406. In some embodiments, the tangs 2406 are positioned around the top perimeter of one or more of the tabs 2404. Alternatively, the tangs 2406 are able to be positioned elsewhere on one or more of the tabs 2404 such that the tangs 2406 are able to increase the surface area of the tabs 2404. In some embodiments, one or more of the tangs 2406 are able to extend beyond the perimeter of the body 2402. In such embodiments, when the tab 2404 is retracted within the body 2402, a portion of the extended tangs 2406 would be housed within the tang recesses 2408 and a portion of the tangs 2406 would protrude out of the tang recesses 2408 beyond the perimeter of the body 2402. Although the tangs 2406 and tang recesses 2408 are described in reference to the bone fusion device 2400, it is understood that they are able to be incorporated into the other bone fusion devices described herein.

Figure 7:
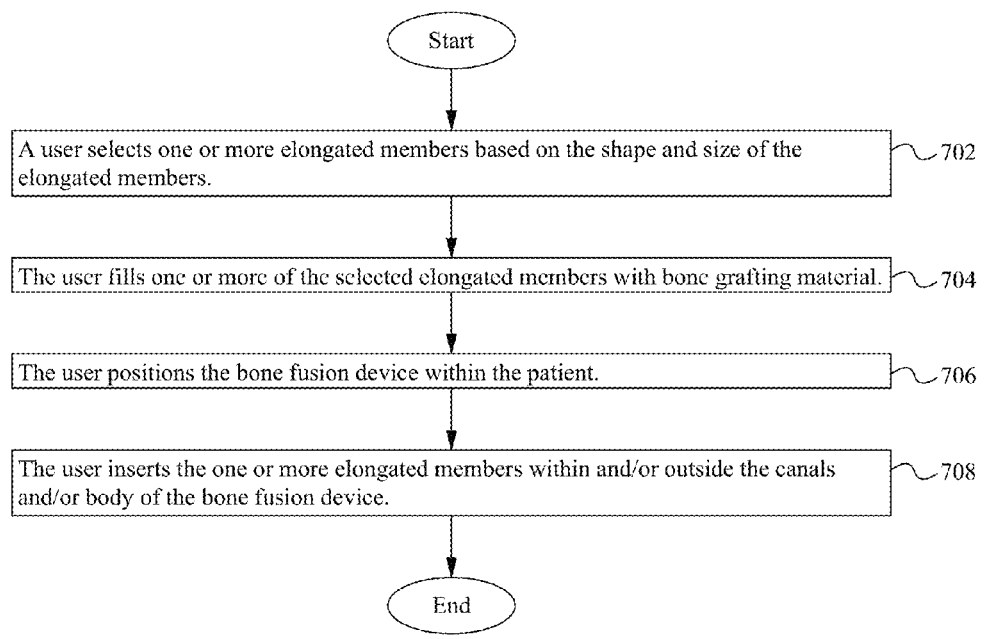
FIG. 7 illustrates a flowchart directed to a method of using the bone fusion system according to some embodiments.

A method of using the bone fusion device 600 according to some embodiments is illustrated by the flow chart in FIG. 7. A user selects one or more elongated members 623 based on the shape and size of the elongated members 623 at the step 702. Alternatively, the user selects one or more elongated members 623 and bends them into a desired shape and size. The user fills one or more of the selected elongated members 623 with bone grafting material at the step 704. The user positions the bone fusion device 600 within the patient at the step 706. The user inserts the one or more elongated members 623 within and/or outside the canals 621 and/or body 614 of the bone fusion device 600 at the step 708. Alternatively, one or more of the elongated members 623 are able to be positioned within and/or outside of the canals 621 before or during the positioning of the bone fusion device 600 within the patient. Thus, the method of using the bone fusion system provides the advantage of allowing the bone grafting material to be packed into the elongated members 623 and positioned after the positioning of the bone fusion device 600 within the patient. As a result, the bone fusion device 600 is able to prevent the elongated members 623 from being moved during the positioning of the bone fusion device within the patient thereby keeping the bone grafting material in the desired position and/or shape with respect to the adjacent bones and bone fusion device 600 such that quicker and stronger bone fusion is promoted speeding up the healing process. In some embodiments, one or more of the steps of the above method are able to be omitted or combined with the other methods described herein.

Figures 8A, 8B:
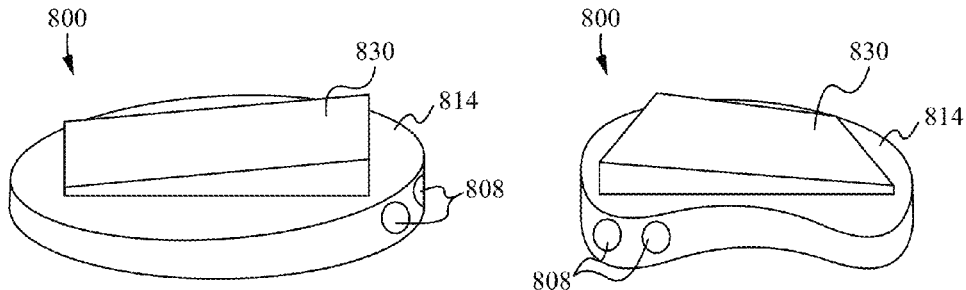
FIG. 8A illustrates a top view of a bone fusion device according to some embodiments.
FIG. 8B illustrates a top view of a bone fusion device according to some embodiments.
Figure 8C:
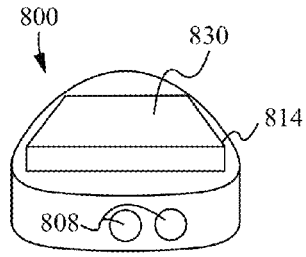
FIG. 8C illustrates a top view of a bone fusion device according to some embodiments.
Figure 8D:
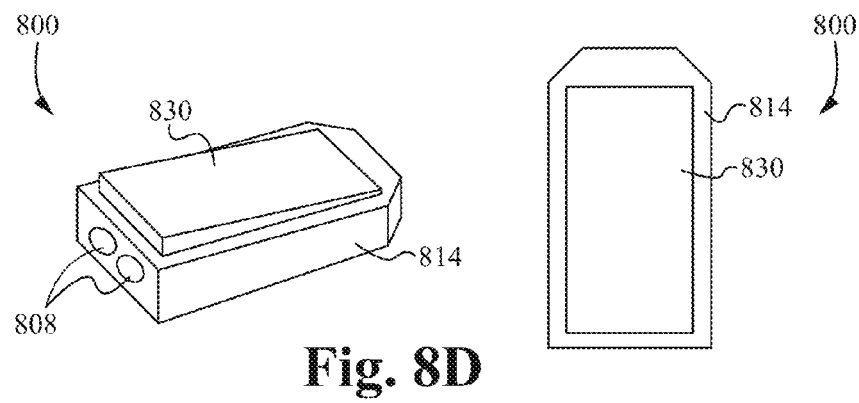
FIG. 8D illustrates a top and perspective view of a bone fusion device according to some embodiments.
Figure 8E:
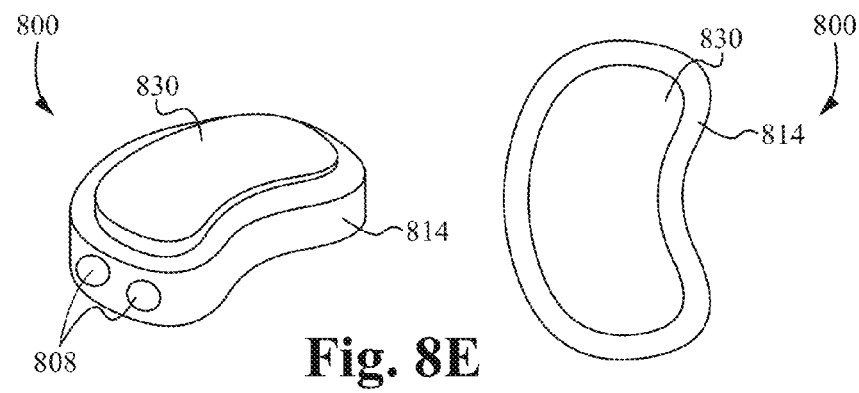
FIG. 8E illustrates a top and perspective view of a bone fusion device according to some embodiments.
Figure 8F:
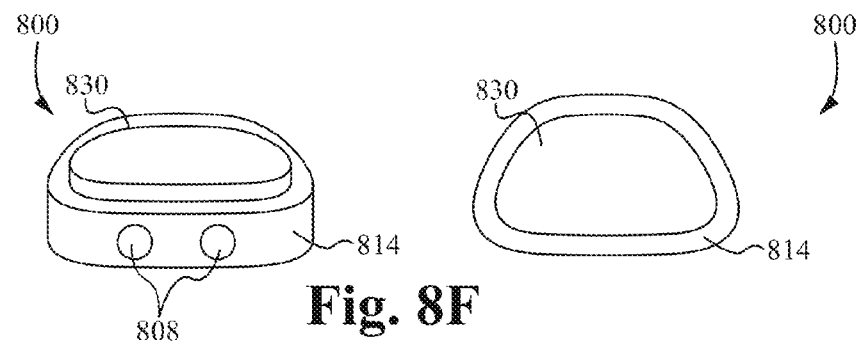
FIG. 8F illustrates a top and perspective view of a bone fusion device according to some embodiments.
Figure 8G:
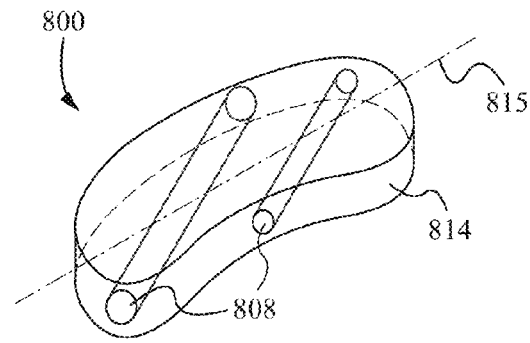
FIG. 8G illustrates a perspective view of a bone fusion device according to some embodiments.

FIGS. 8A-8G illustrate top and perspective views of a bone fusion device 800 according to some embodiments. Although one or more of the components discussed above are omitted, the bone fusion devices 800 shown in FIGS. 8A-8G are substantially similar to the bone fusion device 100 except for the differences described herein. As shown in FIGS. 8A-8G, the bone fusion device 800 comprises drive screws 808 one or more tabs 830 and a body/frame 814. Specifically, the body 814 comprises an oval shaped (FIG. 8A), kidney shaped (FIG. 8B), round shaped (FIG. 8C), rectangular shaped (FIG. 8D), banana shaped (FIG. 8E) or otherwise shaped (FIG. 8F) top/bottom profile such that the shape of the top/bottom profile of the body 814 is substantially similar to the shape of the horizontal profile of one or more vertebrae. Alternatively, the top/bottom profile of the body 814 is able to comprise one or more other shapes that substantially match bones that are to be fused to the bone fusion device 800. Alternatively, the top profile of the tabs 830 are able to be shaped as described herein, wherein the body 814 remains the standard shape as described above. In some embodiments, the top profile of the tabs 830 are shaped substantially similar to the top/bottom profile of the body 814. For example, as shown in FIGS. 8D-8F, the tabs 830 have rounded edges to match the perimeter of the frames 814. Alternatively, the top profile of the tabs 830 is able to comprise other shapes as are well known in the art. In some embodiments, the top profile shapes of the body 814 are between 15 and 25 mm along the anterior/posterior axis and between 20 and 45 mm along the lateral axis. Alternatively, other dimensions are envisioned. For example, for bone fusion devices designed for cervical spinal bones, the body 814 is able to be less than 15 mm along the anterior/posterior axis and less then 20 mm along the lateral axis. Alternatively, the body 814 is able to be 55 mm or longer along the lateral axis (typically for extreme lateral lumbar interbody fusion). In some embodiments, the body 814 and/or tab 830 have an angled upper surface such that the angle of the bone fusion device 800 matches the angle between the vertebrae. In some embodiments, the angle is equal to 15 degrees. Alternatively, other angles are able to be utilized. In some embodiments, as shown in FIG. 8G, the drive screws 808 are able to be non-parallel with the elongated top dimension/axis 815 of the body 814.

As a result, the bone fusion device 800 provides the advantage of substantially matching the horizontal profiles of the bones to be fused, thereby increasing the strength and efficiency of the fusion process. Further, the profile shapes provide the advantage of enabling a user to select a bone fusion device 800 with a top profile shape whose orientation matches the insertion orientation of the operation. Additionally, the angles at which the drive screws 808 are oriented with respect to the elongated axis 815 of the body 814 is able to be selected to match the angle of access provided by a desired operation. As a result, the bone fusion device 800 does not need to be turned to be in the proper orientation between the bones of the patient whether the procedure is anterior, posterior, lateral, far-lateral or transforaminal lumbar interbody fusion. Moreover, the upper surface angles provide the advantage of enabling a user to select a bone fusion device 800 with a body 814 and/or tab 830 angle that matches the angle between the target vertebrae.

Figure 9:
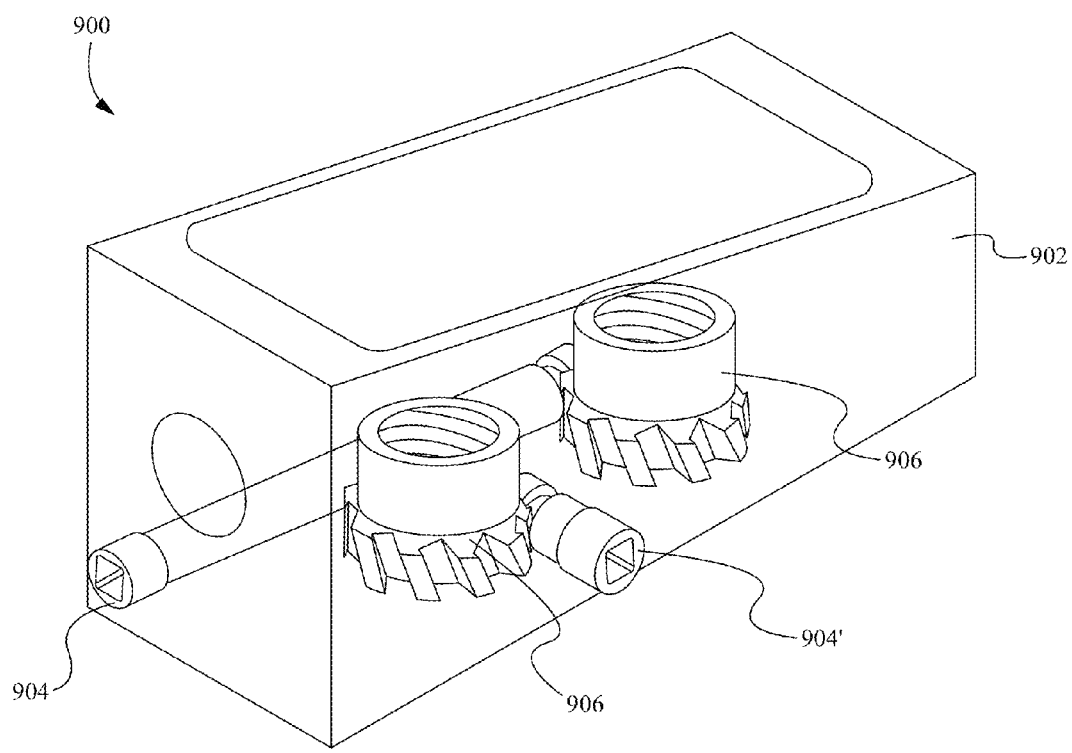
FIG. 9 illustrates a cross sectional perspective view of a bone fusion device having one or more angled drive screws according to some embodiments.

FIG. 9 illustrates a cross sectional perspective view of a bone fusion device 900 having one or more angled drive screws according to some embodiments. The bone fusion device 900 shown in FIG. 9 is substantially similar to the bone fusion device 100 except for the differences described herein. Specifically, as shown in FIG. 9, the bone fusion device 900 comprises a body 902 housing one or more drive screws 904, 904' and one or more gears 906. At least one of the drive screws 904' is able to be angled with respect to the elongated dimension of the body 902 while still operable coupled with one of the gears 906. Alternatively, a plurality or all of the drive screws 904, 904' are able to be angled or non-parallel with respect to the elongated dimension of the body 902. As a result, a user is able to control the extension, retraction and angle adjustment of the tab (not shown) by rotating the gears 906 using the drive screws 904, 904'. In some embodiments, the angled drive screws 904' are positioned such that the drive screw 904 is substantially perpendicular to the elongated dimension of the body 902. Alternatively, the angled drive screws 904' are able to be positioned such that they each form any angle with the elongated dimension of the body 902 while still operably coupled to one of the gears 906. Thus, the bone fusion device 900 provides the advantage of allowing the tab to be extended/retracted and/or the angle of the tab adjusted from angles other than parallel to the elongated dimension of the body, which is critical in procedures where the device 900 is to be inserted from varying angles such as, for example, anterior lumbar interbody fusion, lateral lumbar interbody fusion or transforaminal lumbar interbody fusion. Additionally, the differences to the bone fusion device 900 described in FIG. 9 are able to be incorporated with and/or replace components of each of the other bone fusion devices described herein.

Figure 10:
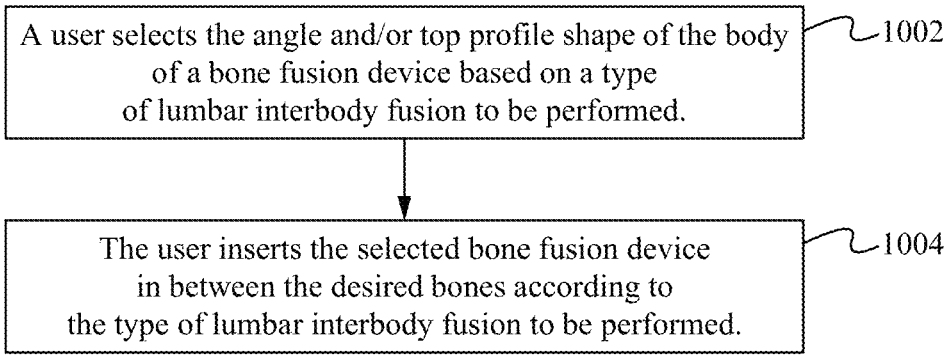
FIG. 10 illustrates a flowchart directed to a method of using a bone fusion device according to some embodiments.

A method of using the bone fusion device 800 according to some embodiments is illustrated by the flow chart in FIG. 10. A user selects the body angle and/or top profile shape of a bone fusion device 800 based on a type of lumbar interbody fusion to be performed at the step 1002. In some embodiments, the user selects an elongated oval shape body 814 based on the type being extreme lateral lumbar interbody fusion. Alternatively, the user selects a kidney or rounded shape body 814 based on the type being anterior lumber interbody fusion. In some embodiments, the user selects the shape of the top profile of the body 814 of a bone fusion device 800 based on a horizontal profile of the bone or bones to be fused to the device. For example, a bone fusion device is able to be selected because the device 800 has a top profile shape that substantially matches the shape of the horizontal profile of a cervical spinal bone or bones to be fused with. The user inserts the selected bone fusion device 800 in between the desired bones according to the type of lumbar interbody fusion to be performed at the step 1004. In some embodiments, the bone fusion device 600 is able to be positioned offset from the center of the adjacent bones and/or discs. Thus, the method of using the bone fusion device 600 provides the advantage of enabling a user to select a device 800 with desired dimensions of angle and/or top profile based on the type of procedure thereby increasing the effectiveness of the procedure. Additionally, it should be noted that one or more of the steps of the above method are able to be omitted or combined with the other methods described herein.

Figure 11:
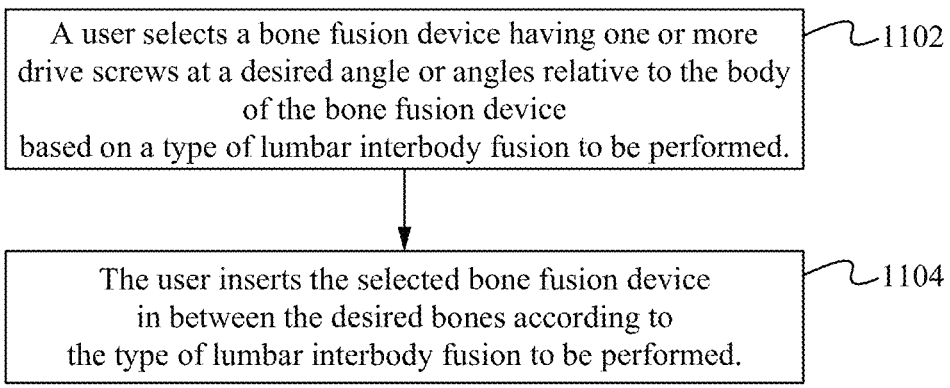
FIG. 11 illustrates a flowchart directed to a method of using a bone fusion device according to some embodiments.

A method of using the bone fusion device 900 according to some embodiments is illustrated by the flow chart in FIG. 11. A user selects a bone fusion device 900 having one or more drive screws 904, 904' at a desired angle relative to the elongated dimension of the body 902 of the device 900 based on a type of lumbar interbody fusion to be performed at the step 1102. In some embodiments, the user selects angled drive screws 904' that are substantially parallel to the elongated dimension of the body 902 based on the type being anterior lumbar interbody fusion. In some embodiments, the user selects a bone fusion device 900 having angled drive screws 904' at a desired angle relative to the elongated dimension of the body 902 based on the shape of the top profile of the body 902 of a bone fusion device 900 and the type of lumbar interbody fusion to be performed. The user inserts the selected bone fusion device 900 in between the desired bones according to the type of lumbar interbody fusion to be performed at the step 1104. Thus, the method of using the bone fusion device 900 provides the advantage of enabling a user to select a bone fusion device 900 having angled drive screws 904' that form a desired angle with the elongated dimension of the body 902 of the bone fusion device 900 based on the type of procedure thereby increasing the effectiveness of the procedure. In some embodiments, one or more of the steps of the above method are able to be omitted or combined with the other methods described herein.

Figure 12:
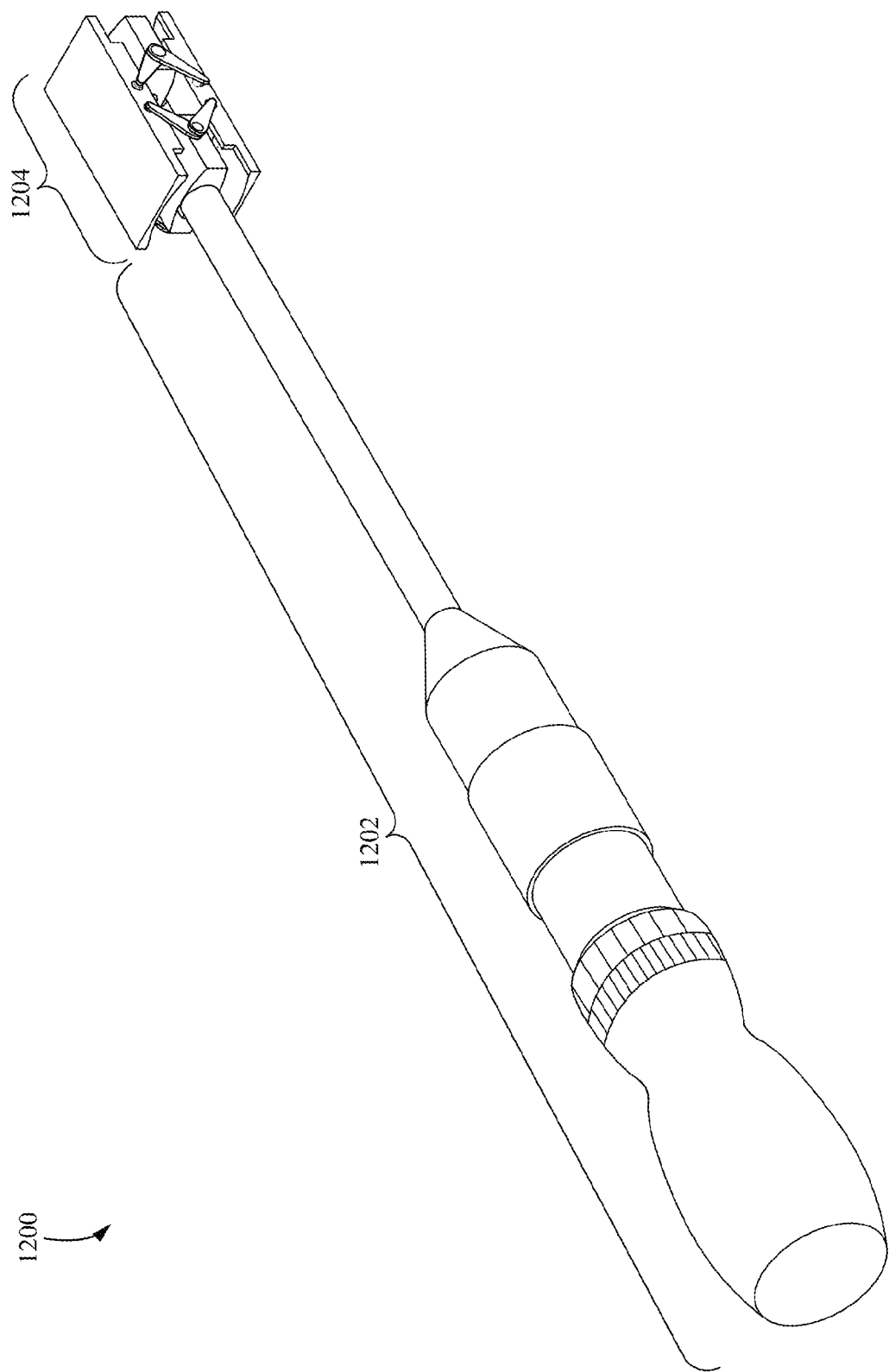
FIG. 12 illustrates a perspective view of a distraction instrument for measuring the space to be filled by a bone fusion device according to some embodiments.
Figure 13:
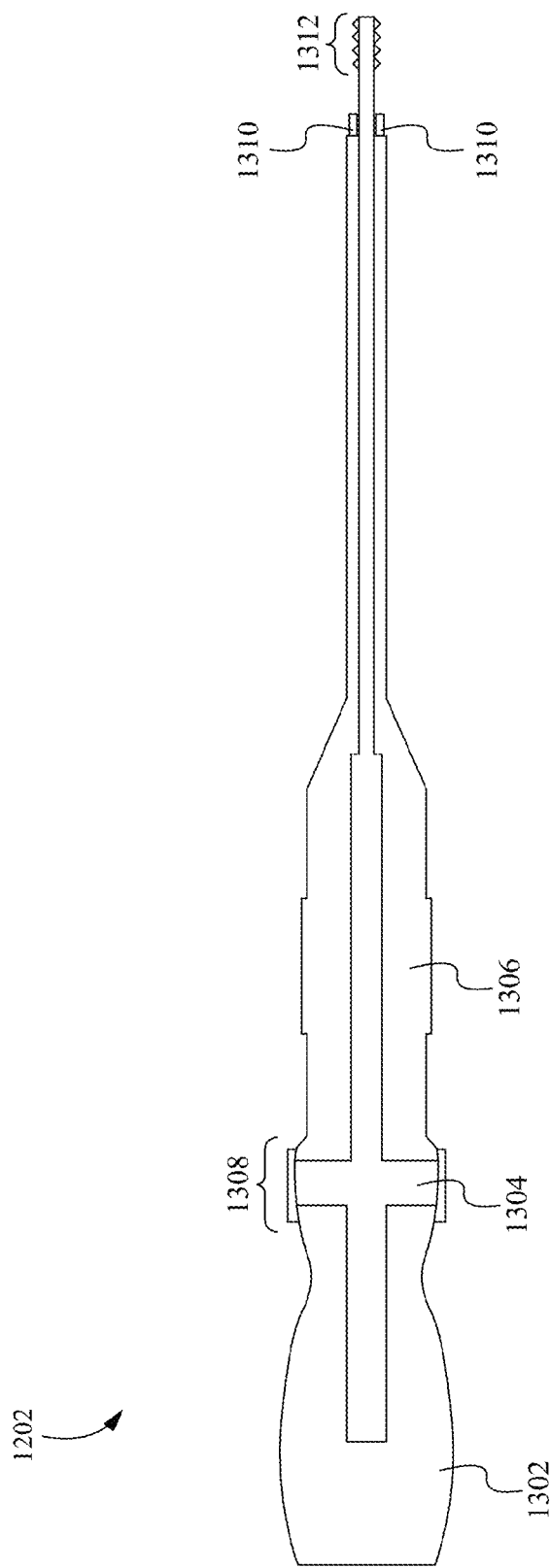
FIG. 13 illustrates a top cross sectional view of the distraction body according to some embodiments.

FIG. 12 illustrates a perspective view of a distraction instrument 1200 for measuring the space to be filled by a bone fusion device according to some embodiments. As shown in FIG. 12, the distraction instrument 1200 comprises a distraction body 1202 and a distraction head 1202 operably coupled together. FIG. 13 illustrates a top cross sectional view of the distraction body 1202 according to some embodiments. As shown in FIG. 13, the distraction body 1202 comprises a handle 1302, a engaging element 1304 and a guide element 1306. The handle 1302 is coupled with the engaging element 1304 which is positioned within the guide element 1306 such that a user is able to rotate, push and/or pull the handle 1302 in order to rotate, extend and/or retract the engaging element 1304 within or further out of the guide element 1306. In some embodiments, the handle 1302 and/or guide element 1306 comprise one or more gripping ridges enabling a user to rotate or otherwise move the handle 1302 with respect to the guide element 1306 without slipping. In some embodiments, the instrument 1200 is able to comprise an electric motor and control interface (not shown) such that the movement of the handle 1302 is able to be effectuated by a user controlling the operation of the electric motor via the control interface. In some embodiments, the guide element 1306 comprises one or more a stop pins 1310 that couple to the stop apertures 1417 of the rear fitting 1414 of the rear jack assembly 1404 (see FIG. 14). When coupled within the stop apertures 1417, the stop pins 1310 are able to prevent the distraction head 1202 from rotating with the engaging element 1304 as well as keeping the rear fitting 1414 of the rear jack assembly 1404 abut the end of the guide element 1306. In some embodiments, the engaging element 1304 comprises a threaded portion 1312 positioned along the end of the engaging element 1304 such that the threaded portion 1312 is able to operably coupling with the threads 1418 of the front fitting 1415 of the front jack assembly 1406 (see FIG. 14). As a result, when the engaging element 1304 is rotated, the threaded portion 1312 is able to engage the threads 1418 of the front fitting 1415 causing the front fitting 1415 to slide toward or away from the rear fitting 1414. Alternatively, the threaded portion 1312 and the threads 1418 are able to be omitted and the end of the engaging element 1304 is able to be coupled to the front fitting 1415 such that when the engaging element 1304 is pulled into or pushed out of the guide element 1306 the coupling causes the front fitting 1415 to also slide toward or away from the rear fitting 1414. Alternatively, the threaded portion 1312 is a female thread such that when the engaging element 1304 is rotated, the threading 1312 causes the engaging element 1304 to retract into the guide element 1306 and the front fitting 1415 to slide toward the rear fitting 1414. As a result, the engaging element 1304 does not protrude out of the front fitting 1415 during the expanding or contracting of the plates 1402. In such embodiments, the threading 1312, male or female is able to be positioned in other places along the engaging element 1304 and complimenting threading is able to be positioned, for example, within the conduit 1416 of the rear fitting 1414 or within the end of the guide element 1306.

Figure 14:
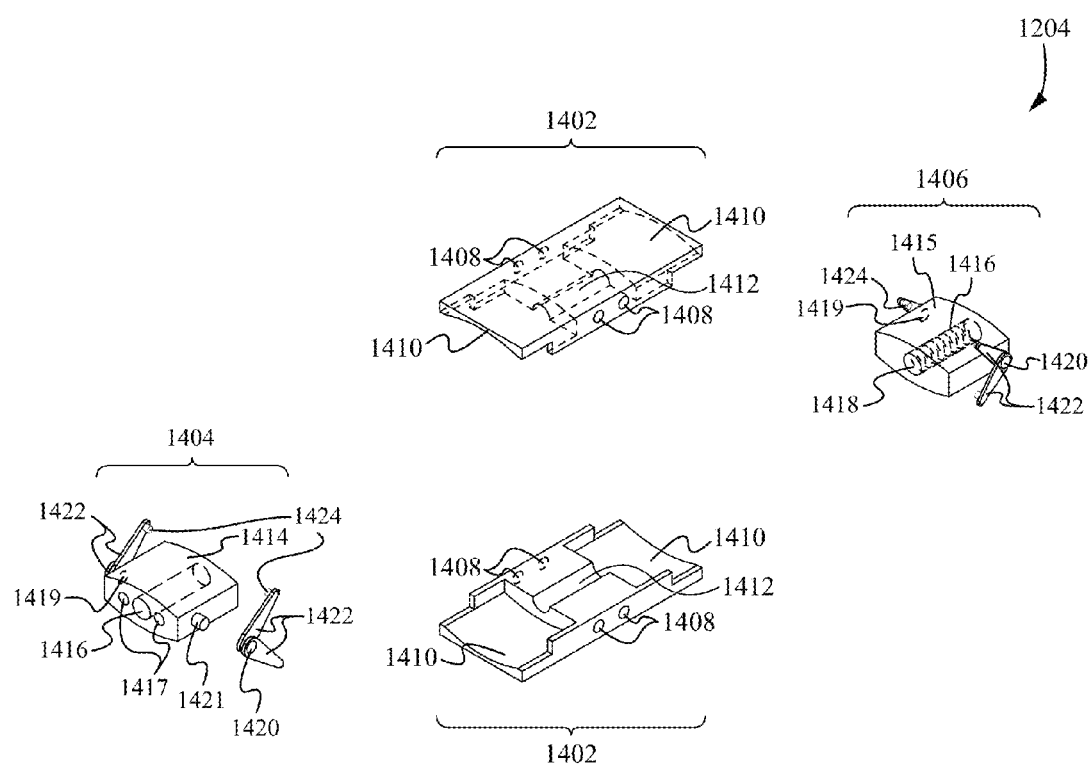
FIG. 14 illustrates a perspective view of the components of the retraction head of the retraction instrument according to some embodiments.

In some embodiments, one or more of the handle 1302, engaging element 1304 and/or the guide element 1306 comprise one or more indicators 1308 that indicate values corresponding to the current separation between the plates 1402 of the head 1204 (see FIG. 14). In some embodiments, the indicators 1308 comprise first markings on the visually exposed surface of the engaging element 1304 and/or handle 1302 that move relative to corresponding second markings on the guide element 1302 when the engaging element 1304 is rotated or otherwise moved. As a result, based on the alignment of the first and second markings the current separation between the plates 1402 of the head 1204 is able to be determined. Alternatively, the indicators 1308 are able to comprise a digital or analog readout/display that indicates the current level of distraction of the instrument 1200. In some embodiments, the motion of the handle 1302 is effectuated by an electrical motor and the indicators 1308 are able to include the control interface for controlling the operation of the electrical motor. Alternatively, other types of indicating elements 1308 corresponding to the current separation of the plates 1402 are able to be used as are well known in the art.

In some embodiments, the indicators 1308 indicate a number of revolutions or rotations that the positioning element of a bone fusion device will require in order to extend the tabs to the height indicated by the separation of the plates 1402. For example, in some embodiments the a user is able to input or the instrument 1200 is able to be pre-programmed with the type of bone fusion device to be used and based on this data, the indicators 1308 are able to indicate the number of rotations/revolutions that the positioning element of a bone fusion device will require in order to extend the tabs to the height indicated by the separation of the plates 1402. In some embodiments, based on the determined current separation of the plates 1402, the indicators 1308 are able to indicate a recommended size and/or type of bone fusion device to be used for filling the measured space. As a result, the distraction instrument 1200 provides the advantage of indicating the best type/size of bone fusion device to use and/or the exact amount of rotation needed to a user of a bone fusion device such that the user does not overextend the tabs of the bone fusion device.

In some embodiments, the instrument 1200 comprises a force measurement component (not shown) and/or the indicators 1308 indicate the amount of force on the plates 1402 that is resisting the expansion/distraction of the plates 1402. In such embodiments, the distraction instrument 1200 is able to be configured to prevent the user from further extending/distracting the plates 1402 when a predefined and/or adjustable force threshold value is detected by the force measurement component. For example, if the distraction is effectuated by an electronically controlled motor the distraction system is able to be configured to automatically stop when the force threshold value is detected. Alternatively, the force measurement component is able to be implemented mechanically such that the components of the instrument 1200 that effectuate the distraction of the plates 1402 prevent further distraction when a predetermined and/or adjustable amount of resistance is present. As a result, the distraction instrument 1200 provides the benefit of enabling a user to manually stop, automatically stopping and/or preventing the user for continuing to distract the plates 1402 when the force measurement component and/or indicators 1308 indicate that a predetermined amount of expansion resistant force is detected on the plates 1402. Thus, the distraction instrument 1200 prevents over distraction that which results in inaccurate measurements and possible injury.

FIG. 14 illustrates a perspective view of the components of the retraction head 1204 of the retraction instrument 1200 according to some embodiments. As shown in FIG. 14, the retraction head 1204 comprises a pair of retraction plates 1402 coupled together by a rear jack assembly 1404 and a front jack assembly 1406. The rear and front jack assemblies 1404, 1405 each comprise a rear/front fitting 1414, 1415 having a fitting conduit 1416 and coupled to a plurality of legs 1422 via one or more fitting pins 1420. Specifically, the plurality of legs 1422 each have a leg pin 1424 and a leg aperture 1419, wherein the leg apertures 1419 are configured to slide onto a pair of fitting protrusions 1421 such that the legs 1422 are able to pivot/rotate about the fitting protrusions 1421 and are prevented from sliding off the protrusions 1421 by the fitting pins 1420. As shown in FIG. 14, two fitting protrusions are each rotatably coupled to a pair of legs 1422. Alternatively, more of less fitting protrusions 1421 are able to be rotatably coupled to more or less legs 1422. Alternatively, the protrusions 1421 and/or fitting pins 1420 are able to be omitted and the legs 1422 are able to be rotatably coupled to the fittings 1414, 1415 via other coupling mechanisms as are well known in the art.

In some embodiments, the conduit 1416 of the rear fitting 1414 is bare whereas the conduit 1416 of the front fitting 1415 has an inner threading 1418 that is operably coupled to the threaded portion 1312 of the engaging element 1304 when the engaging element 1304 is positioned within the conduits 1416 of the retraction head 1204. As a result, the engaging element 1304 is able to freely move independent of the rear fitting 1414, but causes the front fitting 1415 to move toward or away from the rear fitting 1414 along the engaging element 1304 when rotated. Alternatively, the threading 1418 of the conduit 1416 of the front fitting 1415 is able to be omitted and the engaging element 1304 is able to be otherwise coupled to the front fitting 1415 such that when the engaging element 1304 is pulled into or pushed out of the guide element 1306 the coupling causes the front fitting 1415 to correspondingly slide toward or away from the rear fitting 1414. In some embodiments, the rear fitting 1414 comprises one or more stop apertures 1417 that couple with the stop pins 1310 in order to prevent the distraction head 1202 from rotating with the engaging element 1304 and to keep the rear fitting 1414 of the rear jack assembly 1404 in contact with the end of the guide element 1306. Alternatively, the stop pins 1310 and stop apertures 1417 are able to be omitted and the rear fitting 1414 is able to be coupled to the guide element 1306 via other coupling mechanisms as are well known in the art.

The retraction plates 1402 each comprise one or more leg pin apertures 1408, a pair of fitting cavities 1410 and a plate channel 1412. The leg pin apertures 1408 are configured to rotationally couple to the leg pins 1424 such that the plates 1402 are coupled together via the front and rear jack assemblies 1404, 1406. Specifically, when the legs 1422 are caused to rotate about the protrusions 1421 (due to movement of the engaging element 1304), the legs 1422 also rotate within the leg pin apertures 1408 about the leg pins 1424 causing the plates 1402 to selectively move apart or come together. When the plates 1402 are positioned together the fitting cavities 1410 and plate channels 1412 of the upper plate 1402 align with the fitting cavities 1410 and plate channel 1412 of the lower plate 1402. As a result, the height of the retraction head 1204 in the retracted position is minimized because the rear and front fittings 1414, 1415 are able to fit within the aligned fitting cavities 1410 and the engaging element 1412 is able to fit within the aligned plate channels 1412. This provides the advantage of minimizing the size of the required surgical incision for the bone fusion surgery measurement operation.

Figure 15A:
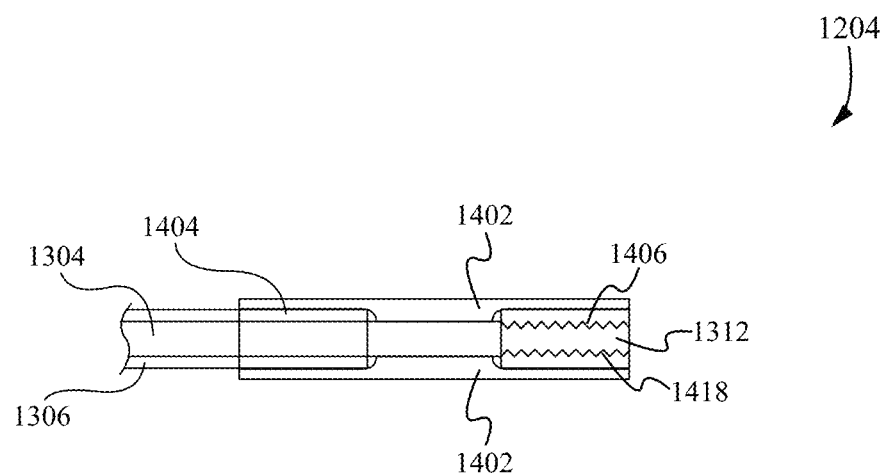
FIG. 15A illustrates cross sectional view of the head of the retraction instrument with the plates fully retracted according to some embodiments.
Figure 15B:
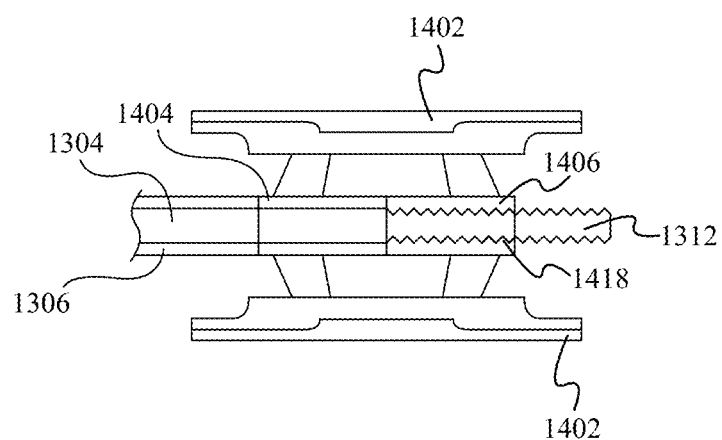
FIG. 15B illustrates cross sectional view of the head of the retraction instrument with the plates fully extended according to some embodiments.

FIGS. 15A and 15B illustrate cross sectional view of the head 1204 of the retraction instrument 1200 with the plates 1402 fully retracted and fully extended, respectively, according to some embodiments. As shown in FIG. 15A, when the retraction instrument 1200 is in the retracted position, the plates 1402 are in contact such that the fittings 1414, 1415 are all or partially housed within/between the plates 1402. While in this position, the retraction instrument 1200 creates the smallest profile possible and thus is able to be surgically inserted between two vertebrae of a patient with a minimally invasive procedure. As shown in FIG. 15B, once in position, the user is able to rotate or otherwise move the engaging element 1304 within the guide element 1306 and head 1204 by manipulating the handle 1302. This manipulation causes the front fitting 1415 to selectively move closer to the rear fitting 1414 and correspondingly the plates 1402 to move away from each other until the desired measurement has been made or the maximum height has been reached due to the front fitting 1415 contacting the rear fitting 1414 along the engaging element 1304. The, user is then able to retract the plates 1402 back together for removal using the opposite rotation and/or opposite other movement of the engaging element 1304 via the handle 1302. Accordingly, the retraction instrument 1200 provides the advantage of a minimized retracted profile that enables a surgeon to measure the size of the space needed to be filled by a bone fusion device or other device while minimizing the surgical incision required to take the measurement.

Figure 16:
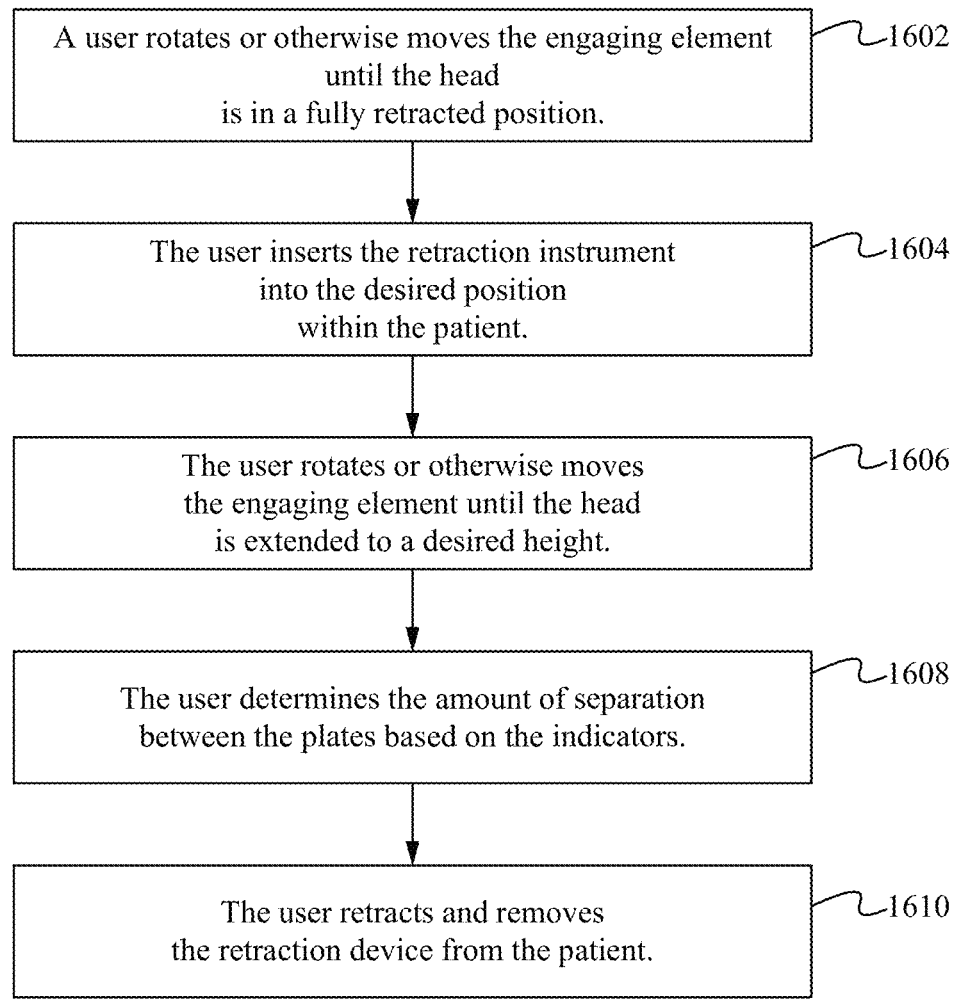
FIG. 16 illustrates a flow chart of a method of operating the retraction instrument according to some embodiments.

FIG. 16 illustrates a flow chart of a method of operating the retraction instrument 1200 according to some embodiments. A user rotates or otherwise moves the engaging element 1304 until the head 1204 is in a fully retracted position at the step 1602. The user inserts the retraction instrument 1200 into the desired position within the patient at the step 1604. In some embodiments, the desired position comprises between or adjacent to one or more vertebrae. In some embodiments, the retraction instrument 1200 is inserted anteriorly. Alternatively, the retraction instrument 1200 is able to be inserted posteriorly, lateral, far-lateral or transforaminaly. The user rotates or otherwise moves the engaging element 1304 until the head 1204 is extended to a desired height at the step 1606. In some embodiments, the desired height comprises the height required such that the lower and upper plates 1402 abut the vertebrae. The indicators 1308 indicate the amount of separation between the plates 1402 at the step 1608. In some embodiments, the indicators 1308 indicate a type and/or size of bone fusion device to utilize to fill the measured space. In some embodiments, the indicators 1308 indicate a number of rotations/revolutions that the positioning element of a bone fusion device will require in order to extend the tabs to the height indicated by the amount of separation of the plates 1402. In some embodiments, the indicators 1308 indicate the current amount of expansion resisting force on the plates 1402. In some embodiments, the desired height comprises the height or separation of the lower and upper plates 1402 when the indicators 1308 indicate the plates 1402 are experiencing a predetermined expansion resisting force threshold value. The user retracts and removes the retraction device 1200 from the patient at the step 1610. In some embodiments, the user then inserts the a bone fusion device into the desired position and extends the tabs such that the bone fusion device fills the indicated height. In some embodiments, the user extends the tabs such that the bone fusion device fills the indicated height by rotating the positioning element of the bone fusion device a number of times indicated by the indicators 1308. In some embodiments, the bone fusion device inserted was selected based on size and/or type of bone fusion device indicated by the indicators 1308. Therefore, the retraction instrument 1200 provides the advantage of determining the size of the space within the patient while only requiring a small incision and minimally invasive (arthroscopic) surgical procedure which advantageously promotes health and rapid recovery by the patient. Further, by determining the size of the space to be filled, the instrument 1200 provides the advantage of enabling the user to select a bone fusion device of the appropriate size to fit within the space and enables the user to pre-configure the tabs of the bone fusion device to near the height required to fill the space such that minimal extension of the tabs is required when the device is in place within the patient.

Figure 17A:
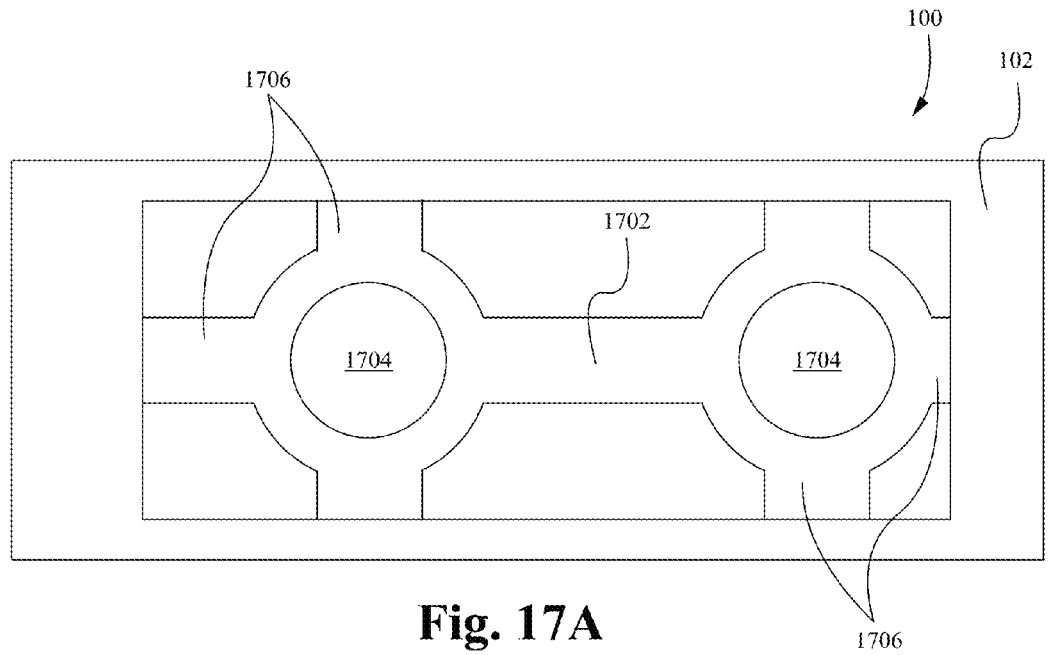
FIG. 17A illustrates a top view of the bone fusion device comprising a webbing according to some embodiments.
Figure 17B:
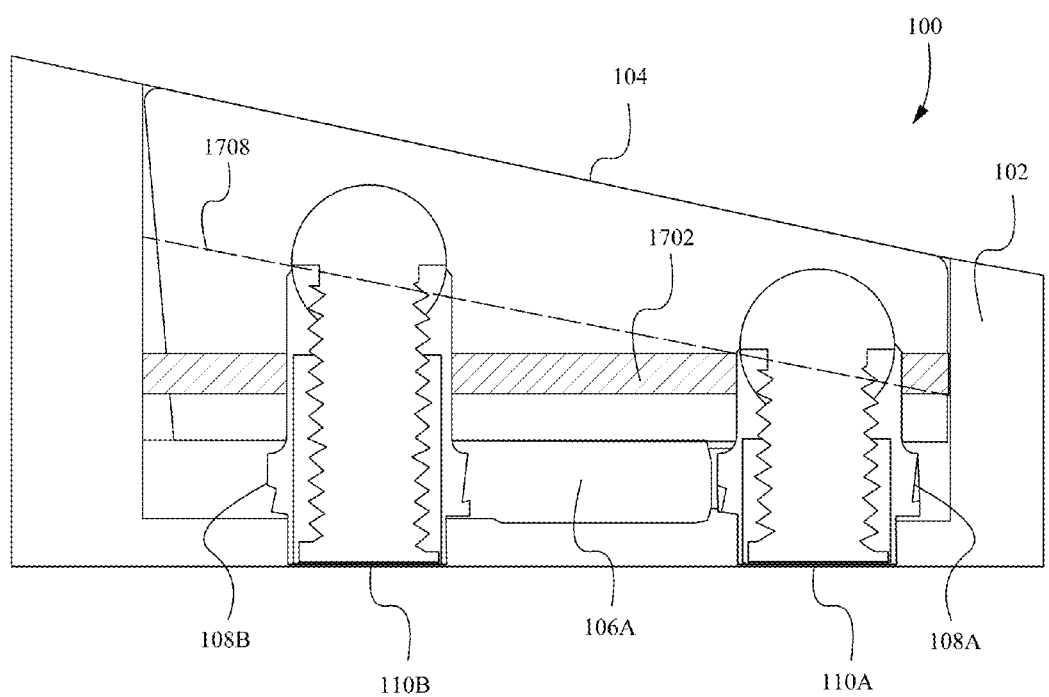
FIG. 17B illustrates a cross-sectional side view of the bone fusion device comprising a webbing according to some embodiments.

FIGS. 17A and 17B illustrate a top and cross-sectional side view of the bone fusion device 100 comprising a webbing 1700 according to some embodiments. As shown in FIGS. 17A and 17B, the webbing 1700 comprises a webbing body 1702 having at least one webbing aperture 1704 for each jack 110A, 110B and one or more bracing members 1706. Specifically, the webbing apertures 1704 are sized such that the jacks 110A, 110B fit snugly within the webbing apertures 1704 and the bracing members 1706 are sized such that they are able to brace the webbing 1700 against the inner walls of the body 102 when the jacks 110A, 110B are within the webbing apertures 1704. As a result, the webbing 1700 is able to support the jacks 110A, 110B such that the jacks 110A, 110B are restricted from moving along the plane of the webbing 1700 (e.g. laterally). In some embodiments, as shown in FIG. 17B, the webbing 1700 is able to be positioned substantially parallel or orthogonal to the bottom of the device body 102. Alternatively, the webbing 1700 is able to be positioned at an angle 1708 in any direction with respect to the plane formed by the bottom of the device body 102. In some embodiments, the webbing body 1702 is substantially planar. Alternatively, the webbing body 1702 is able to have bends and/or curves in order to better fit within the body 102 and/or support the jacks 110A, 110B. Alternatively, the webbing body 1702 is able to extend to the bottom of the inner surface of the body 102 such that the webbing body 1702 is seated on the bottom of the inner surface of the body 102. In such embodiments, the upper surface of the webbing body 1702 is able to be substantially planar or have bends and/or curves in order to better fit within the body 102 and/or support the jacks 110A, 110B. In some embodiments, the bone fusion device 100 is able to comprise a plurality of webbing bodies 1700 positioned at the same or different angles in order to provide increased support to the jacks 110A, 110B. In some embodiments, the webbing body 1702 comprises elastic materials such that as the jacks 110A, 110B move and apply force to the webbing body 1702, the webbing body 1702 resists the movement along the plane of the webbing 1700 as the movement increases and springs the jacks 110A, 110B back in place as the force subsides. Alternatively, the webbing body 1702 is able to comprise inelastic or rigid materials such that the jacks 110A, 110B are substantially prevented from moving along the plane of the webbing 1700. Alternatively, the webbing body 1702 is able to comprise both elastic and inelastic material such that the elastic portions allow some movement of the jacks 110A, 110B, but the inelastic portions limit the extent of this movement. Although the webbing 1700 is shown in FIG. 17A as comprising six bracing members 1706, it is understood that any number of bracing members 1706 are able to be used and each is able to be of varying sizes and positioned along any portion of the perimeter of the webbing 1700. For example, the webbing body 1702 is able to comprise a single bracing member 1706 that forms the entire perimeter of the webbing 1700 and abuts the inner perimeter of the device body 102. Also, although the webbing 1700 is described in reference to the bone fusion device 100, it is understood that the webbing 1700 is able to be used in conjunction with the other bone fusion devices described herein.

Figure 18A:
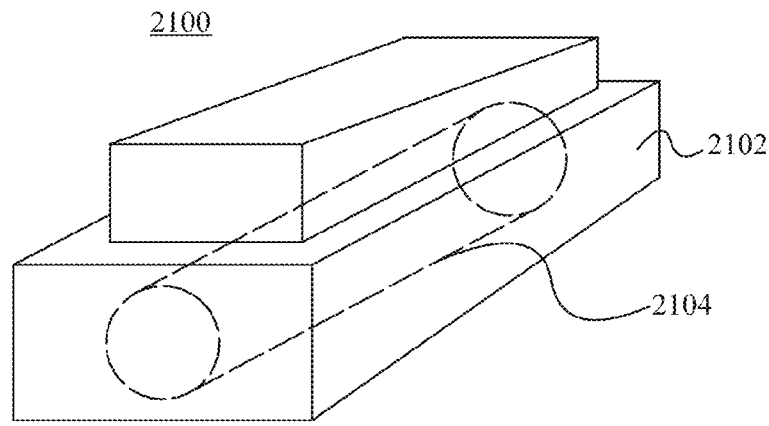
FIG. 18A illustrates a perspective view of a bone fusion system according to some embodiments.
Figure 18B:
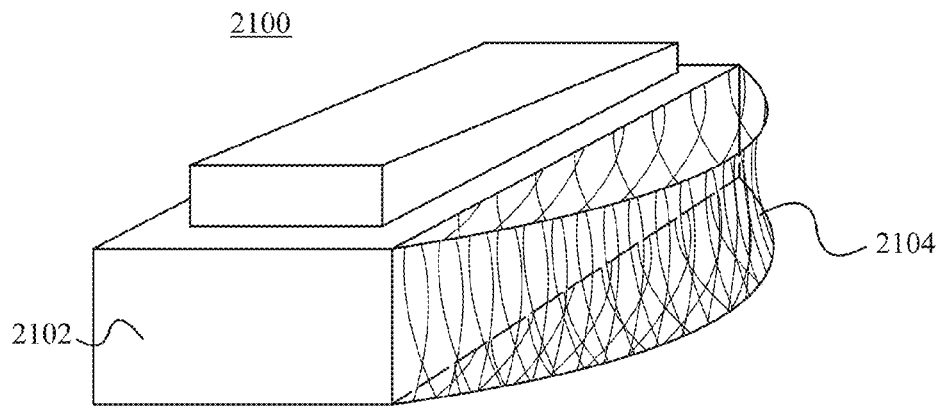
FIG. 18B illustrates a perspective view of a bone fusion system according to some embodiments.
Figure 19:
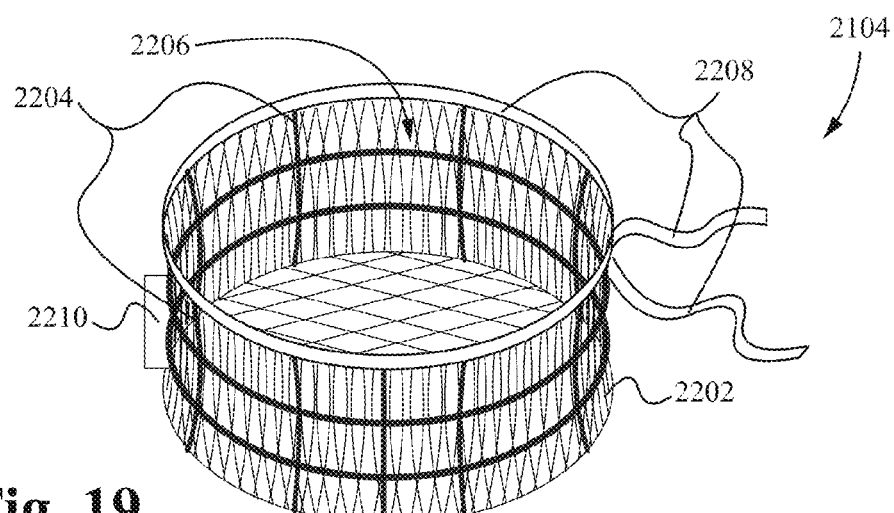
FIG. 19 illustrates a perspective view of a bone grafting material bag according to some embodiments.

FIGS. 18A and 18B illustrate perspective views of a bone fusion system 2100 according to some embodiments. The bone fusion devices 2102 shown in FIGS. 18A and 18B are substantially similar to the bone fusion device 100 except for the differences described herein. The bone fusion system 2100 comprises one or more bone fusion devices 2102 and one or more bone grafting material bags 2104. As shown in FIG. 18A, the bone grafting material bags 2104 are able to be positioned and/or coupled within the bone fusion device 2102. Additionally, as shown in FIG. 18B, the material bags 2104 are also able to be positioned or coupled outside of the bone fusion device 2102. FIG. 19 illustrates a perspective view of a bone grafting material bag 2104 according to some embodiments. As shown in FIG. 19, the material bag 2104 comprises a mesh frame 2202, one or more support bars 2204, at least one opening 2206 for filling the bag 2104 with bone graft material, one or more bag fasteners 2208 and one or more bag coupling elements 2210. In some embodiments, the support bars 2204, bag fasteners 2208 and/or bag coupling elements 2210 are able to be omitted. The support bars 2204 couple to the mesh frame 2202 in order to help the mesh frame 2202 maintain its shape. In some embodiments, the shape of the mesh frame 2202 is a cylinder (as shown in FIGS. 18A and 19). Alternatively, the shape of the mesh frame 2202 is able to be a "half-moon" prism (as shown in FIG. 18B) or other shapes capable of holding a volume of bone grafting material as are well known in the art. In some embodiments, the support bars 2204 comprise polymeric materials such that the support bars 2204 are able to maintain the shape of the material bag 2104. Alternatively, the support bars 2204 are able to comprise other materials capable of supporting the shape of the bag 2104 as are well known in the art.

The opening 2206 enables bone grating material to be packed into the bone grafting material bag 2104 and is able to vary in size based on the size of the mesh frame 2202. The bag fastener 2208 is positioned on the mesh frame 2202 such that the bag fastener 2208 is able to releasably close or fasten the opening 2206 shut such that bone grafting material within the material bag 2104 is unable to escape through the opening 2206. In some embodiments, the bag fastener 2208 comprises a hoop around the opening 2206 and a cinch cord to selectively cinch closed the opening 2206. Alternatively, the bag fasteners 2208 are able to comprise other types of fastening means as are well known in the art. In some embodiments, the material bags 2104 are able to comprise a plurality of openings 2206 and at least one bag fastener 2208 for each opening. The bag coupling element 2210 enables the material bag 2104 to be coupled to one or more bone fusion devices 2102 and/or other material bags 2104. As a result, the bone fusion system 2100 provides the advantage of enabling the user to physically pack a material bag 2104 full of bone grafting material in order to maximize the amount of grafting material provided to the bones. Further, the system 2100 provides the advantage of keeping the bone grafting material in the desired location and shape with respect to the bones to be fused to and/or the position of the bone fusion device 2102 thereby increasing the efficiency of the bone growth and/or healing process. Additionally, it should be noted that one or more of the components of the bone fusion system 2100 are able to be incorporated into the bone fusion system 1000 described above in reference to FIGS. 10-12 and vice versa.

Figure 20:
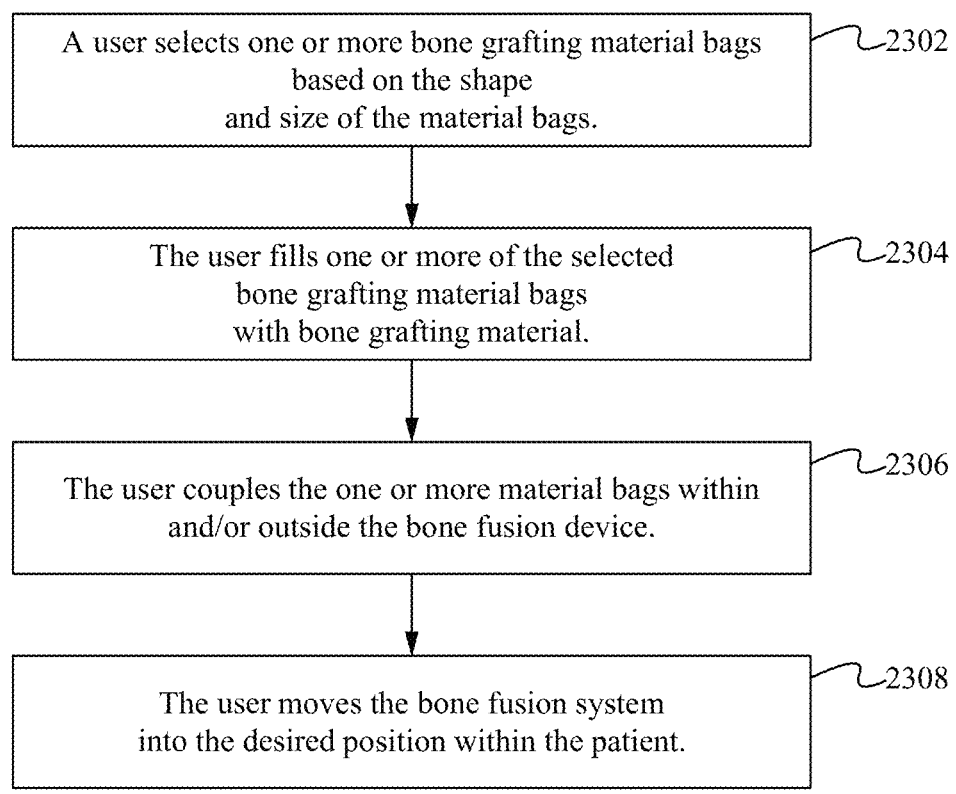
FIG. 20 illustrates a flowchart directed to a method of using the bone fusion system according to some embodiments.

A method of using the bone fusion system 2100 according to some embodiments is illustrated by the flow chart in FIG. 20. A user selects one or more bone grafting material bags 2104 based on the shape and size of the material bags 2104 at the step 2302. The user fills one or more of the selected bone grafting material bags 2104 with bone grafting material at the step 2304. In some embodiments, the material bag 2104 is filled with the bone grafting material with an implement resembling a "caulking gun." Alternatively, the material bag 2104 is able to be filled by a packing element and/or other methods of packing bone grafting material as are well known in the art. The user couples the one or more material bags 2104 within and/or outside the bone fusion device 2102 at the step 2306. The user moves the bone fusion system 2100 into the desired position within the patient at the step 2308. In some embodiments, the material bags 2104 are positioned such that they abut the bones adjacent the bone and/or disc to be replaced. Thus, the method of using the bone fusion system 2100 provides the advantage of allowing the bone grafting material to be packed into the material bags and keeping the bone grafting material in the desired position and/or shape with respect to the adjacent bones and bone fusion device 2102 such that quicker and stronger bone fusion is promoted speeding up the healing process. Additionally, it should be noted that one or more of the steps of the above method are able to be omitted or combined with the other methods described herein.

Figure 22:
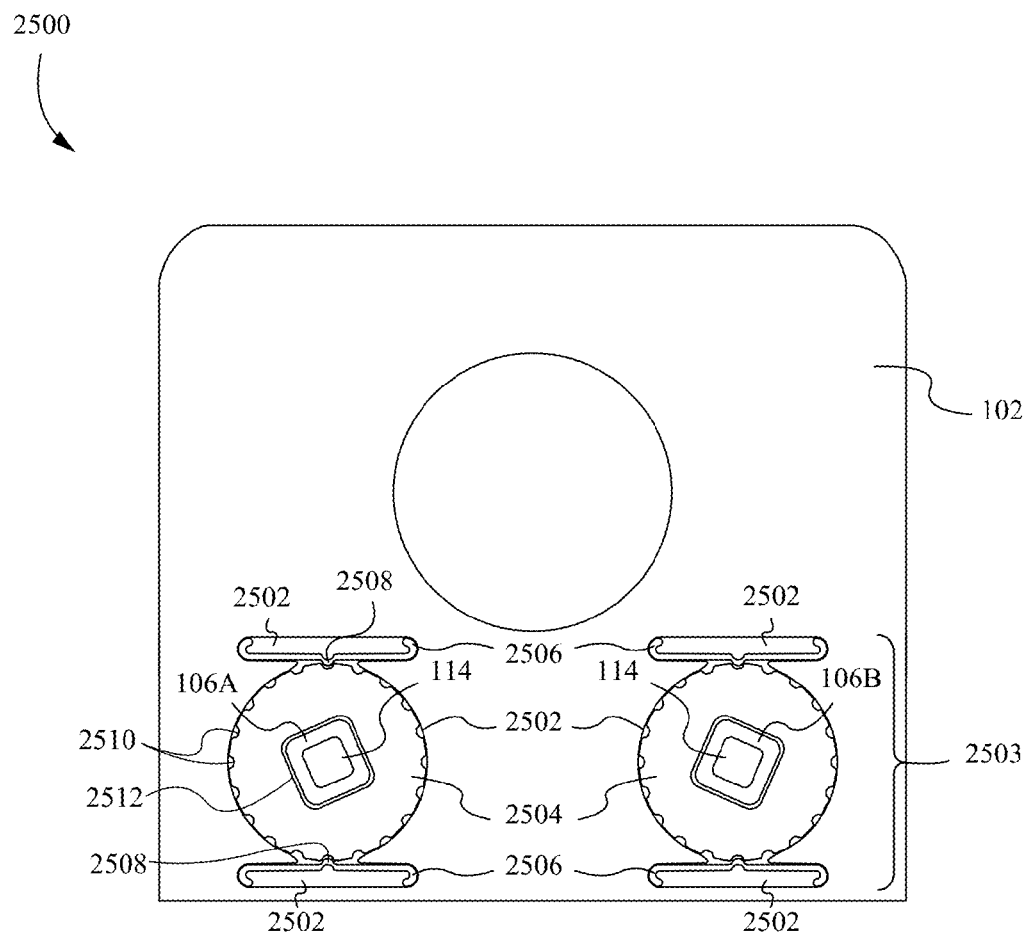
FIG. 22 illustrates a bone fusion device having a position locking mechanism according to some embodiments.

FIG. 22 illustrates a bone fusion device 2500 having a position locking mechanism 2502 according to some embodiments. The bone fusion device 2500 shown in FIG. 25 is substantially similar to the bone fusion device 100 except for the differences described herein. It is noted that the tab 104 of the bone fusion device 2500 have been omitted from FIG. 22 for the sake of clarity. As shown in FIG. 22, the body 102 comprises one or more locking apertures 2502 configured to receive one or more position locking mechanisms 2503, wherein each of the position locking mechanisms 2503 comprise one or more dials 2504 and one or more stoppers 2506. In some embodiments, the device 2500 comprises a locking aperture 2502 and a position locking mechanism 2503 for each tab extension assembly or drive screw 106A, 106B. Alternatively, one or more of the tab extension assemblies or drive screws 106A, 106B are able to have more or less than one locking aperture 2502 and/or position locking mechanism 2503.

The dial 2504 is configured to rotatably fit within the locking apertures 2502 and comprises a dial aperture 2512 and one or more dimples 2510 along the edge or perimeter of the dial 2504. The dial aperture 2512 is able to be sized or otherwise configured to receive an end of one of the drive screws 106A, 106B such that if a drive screw 106A, 106B is within the dial aperture 2512, the end of the drive screw 106A, 106B will cause the dial 2504 to rotate along with the drive screw 106A, 106B. In some embodiments, the drive screw 106A, 106B causes the dial 2504 to rotate by directly physically contacting the dial aperture 2512. Alternatively, the drive screw 106A, 106B is able to cause the dial 2504 to rotate via indirect contact. The one or more dimples 2510 are able to be configured to receive one or more bumps 2508 of the stoppers 2506. In particular, the dimples 2510 are able to have concave dimensions that substantially match convex dimensions of the bumps 2508. The stoppers 2506 are able to be configured to fit within the locking apertures 2502 adjacent to the dial 2504 and comprise one or more bumps 2508. The stoppers 2506, dials 2504 and apertures 2502 are configured such that when within the locking apertures 2502, the stoppers 2506 are adjacent or in contact with the dial 2504 and the bumps 2508 of the stoppers 2506 snap or spring fit within the dimples 2510 of the dial 2504 when a dimple 2510 and a bump 2508 are aligned. Additionally, when a dimple 2510 and a bump 2508 are not aligned, the bump 2508 is compressed against the dimple-less edge of the dial 2504 and primed to spring or decompress into a dimple 2510 when alignment is achieved.

In some embodiments, the dial 2504 is held in place within the locking apertures 2502 by force applied by the bumps 2508 of the stoppers 2506. Alternatively, the dial 2504 is able to be otherwise coupled or uncoupled within the locking apertures 2502 by one or more fastening elements as are well known in the art. In some embodiments, the stoppers 2506 are held in place within the locking apertures 2502 by place holders 2507. In particular, the place holders 2507 are able to be tensioned and/or compressed by the wall of the locking apertures 2502 when the stoppers 2506 are inserted into the locking apertures 2502 and thus provide a spring force against the walls of the locking apertures 2502 to try and relieve that tensioning/compression. Accordingly, the spring force holds the stoppers 2506 within the locking apertures 2502. Alternatively, one or more of the stoppers 2506 are able to be otherwise coupled or uncoupled within the locking apertures 2502 by one or more fastening elements as are well known in the art. Although as shown in FIG. 22, the device 2500 comprises one side of the body 102 including two position locking mechanisms 2503, wherein the position locking mechanisms 2503 comprise a single dial 2504 having sixteen dimples 2510 and two stoppers 2506, it is understood that any of the sides of the body 102 are able to include one or more position locking mechanisms 2503 and the position locking mechanisms 2503 are able to include any number of dials 2504 having any number of dimples 2510 coupled to any number of stoppers 2506.

In operation, as the drive screws 106A, 106B are rotated to extend or retract sides of the tab 104, the dial 2504 is rotated along with the drive screws 106A, 106B and the bumps 2508 compress and decompress into and out of the dimples 2510 as they move in an out of alignment with the bumps 2508. As a result, each point during the rotation of the drive screws 106A, 106B that results in an alignment of a bump 2508 and a dimple 2510 serves as a demarcated degree of rotation and/or degree of extension/retraction of the associated side of the tab 104. In this way, the position locking mechanism 2503 provides the advantage of enabling a user to rotate the drive screws 106A, 106B and thereby extend the sides of the tab 104 to predetermined rotation/extension amounts and/or by predetermined rotation/extension intervals represented by the spacing and number of dimple 2510 and bump 2508 alignment points. For example, the position and/or number of dimples 2510 and/or bumps 2508 of the position locking mechanism 2503 is able to be adjusted to adjust the number and/or position of the alignment points and therefore the number and/or position of plate extension points. Thus, the position locking mechanism 2503 of the bodiless bone fusion device 2500 is able to be tuned to different size devices 2500 based on the number of extension increments needed and the desired extension distance interval between each of the increments. In some embodiments, the increments are configured to be constant. Alternatively, the increments are able to be configured to decrease in size as the sides of the tab 104 approach their maximum extension level. Alternatively, other increment profiles are able to be used as are well known in the art. Further, the compression of the bumps 2508 and their resistance thereto during rotation of the drive screws 106A, 106B between alignment points provides a slipping resistance force the resists unintended rotation of the drive screws 106A, 106B out of an alignment point. As a result, the position locking mechanism 2503 provides the advantage of reducing the chance of the drive screws 106A, 106B unintentionally rotating and/or the sides of the tab 104 unintentionally extending or retracting.

Thus, the bone fusion device, system and method described herein has numerous advantages. First, the bone fusion device, system and method provide the advantage of substantially matching the device or tab top surface profiles with the horizontal profiles of the bones to be fused, thereby increasing the strength and efficiency of the fusion process. As a result, the bone fusion device does not need to be turned to be in the proper orientation between the bones of the patient whether the procedure is anterior, posterior, lateral or transforaminal lumbar interbody fusion. Second, the bone fusion device, system and method provide the advantage of allowing the body to be extended from angles other than parallel to one or more of the drive screws, which is critical in procedures where the device is to be inserted from varying angles. Third, the extension measurement instrument provides the advantage of enabling a user to accurately measure the size of the space to be filled by the bone fusion device thereby allowing the correct bone fusion device to be selected, while also having a minimal profile such that the incision required is minimized. Further, the bone fusion device, system and method provides the advantage of enabling each side of the tab to be individually adjusted such that the side controlled by each assembly is raised or lowered until the desired tab angle is achieved. In this way, the tab is advantageously positioned and angled to correspond to the vertebrae to help brace the device until the bone has fused and to provide a larger surface area to which the bones attach and fuse during a healing period. Moreover, the bone fusion device, system and method provides the advantage of enabling the user to physically pack a material bag full of bone grafting material in order to maximize the amount of grafting material provided to the bones, as well as providing the advantage of keeping the bone grafting material in the desired location and shape with respect to the bones to be fused to and/or the position of the bone fusion device thereby increasing the efficiency of the bone growth and/or healing process. Additionally, the position locking mechanism provides the advantage of reducing the chance of the drive screws unintentionally rotating and/or the sides of the tab unintentionally extending or retracting. Finally, the bone fusion device, system and method provides the advantage of allowing the bone grafting material to be packed into the material bags and keeping the bone grafting material in the desired position and/or shape with respect to the adjacent bones.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention.

What is claimed is:

1. A bone fusion device for insertion into a desired location comprising:
    a body having an interior cavity;
    a tab configured to fit within the interior cavity and selectively move from a retracted position within interior cavity of the body to an extended position extending out of the body;
    a first extension assembly coupled to a first portion of the tab and comprising a first threaded drive mechanism and a first drive screw configured to selectively move the first portion of the tab between the retracted position and the extended position; and
    a second extension assembly coupled to a second portion of the tab and comprising a second threaded drive mechanism and a second drive screw, non-coaxial to the first drive screw, and configured to selectively move the second portion of the tab between the retracted position and the extended position;
    wherein the first drive screw and the second drive screw are independently turned to selectively move the first portion of the tab and the second portion of the tab.

2. The device of claim 1, wherein each of the first and second threaded drive mechanisms comprise a worm gear operably coupled between the drive screw and a support jack such that rotation of the drive screw rotates the worm gear which retracts or extends the support jack into or out of the worm gear.

3. The device of claim 2, wherein at least one of the first and second drive screws is accessible through a first lateral side of the body and at least a second one of the drive screws is accessible through a second lateral side of the body.

4. The device of claim 2, further comprising a support webbing positioned within the inner cavity of the body between one or more walls of the inner cavity and the exterior of the worm gears such that the support webbing resists lateral movement of the worm gears with respect to the walls of the inner cavity.

5. The device of claim 1, wherein the first and second extension assemblies are pivotably coupled to the different portions of the tab such that the tab is able to pivot about the extension assembly.

6. The device of claim 1, wherein the body has a bottom surface and an upper surface, wherein the upper surface is angled with respect to the bottom surface.

7. The device of claim 1, further comprising one or more plugs, wherein the body and the tab comprise one or more holes that extend from outside the device to the inner cavity and are configured to be removably filled by the plugs.

8. The device of claim 7, wherein the plugs comprise bone material.

9. The device of claim 1, wherein the tab comprises one or more tangs positioned along a perimeter of a top surface of the tab and fit within recesses in the top surface of the body when the tab is in the retracted position.

10. The device of claim 9, wherein one or more of the tangs extend from a perimeter of the tab to a perimeter of the body.

11. The device of claim 1, wherein the second drive screw is parallel to the first drive screw.

12. The device of claim 1, wherein the second drive screw is perpendicular to the first drive screw.

13. A bone fusion device for insertion into a desired location comprising:
    a body having an interior cavity;
    a tab configured to fit within the interior cavity and selectively move from a retracted position within interior cavity of the body to an extended position extending out of the body;
    a first extension assembly coupled to a first portion of the tab and comprising a first threaded drive mechanism and a first drive screw having a first longitudinal axis, configured to selectively move the first portion of the tab between the retracted position and the extended position;
    a second extension assembly coupled to a second portion of the tab and comprising a second threaded drive mechanism and a second drive screw having a second longitudinal axis different from the first longitudinal axis, configured to selectively move the second portion of the tab between the retracted position and the extended position; and
    a position locking mechanism operably coupled with each of the first and second extension assemblies and configured to provide a plurality of locking positions that the first and second extension assemblies are biased to stay in by the position locking mechanism.

14. The device of claim 13, wherein each of the first and second threaded drive mechanisms are configured to independently move the first and second portions of the tab between the retracted position and the extended position.

15. The device of claim 14, wherein the position locking mechanism comprises a dial operably coupled with one of the plurality of extension assemblies such that when the one of the plurality of extension assemblies is rotated the dial is also rotated.

16. The device of claim 15, wherein the position locking mechanism comprises one or more stops operably coupled with the dial such that when the one of the first and second extension assemblies is in one of the locking positions the interface between the dial and the stops provides a biasing force that resists the movement of the one of the first and second extension assemblies out of the one of the locking positions.

17. The device of claim 13, wherein the second drive screw is parallel to the first drive screw.

18. The device of claim 13, wherein the second drive screw is perpendicular to the first drive screw.

19. A bone fusion device for insertion into a desired location comprising:
    a body having an interior cavity;
    a tab having a first portion and a second portion, the tab configured to fit within the interior cavity and selectively move from a retracted position within interior cavity of the body to an extended position extending out of the body;

a first extension assembly coupled to the first portion of the tab and configured to move the first portion of the tab between the retracted position and the extended position, the first extension assembly comprising a first drive screw having a first longitudinal axis to control extension of the first extension assembly; and a second extension assembly coupled to the second portion of the tab and configured to move the second portion of the tab between the retracted position and the extended position, the second extension assembly comprising a second drive screw having a second longitudinal axis different from the first longitudinal axis, to control extension of the second extension assembly;

wherein the first drive screw and the second drive screw are independently turned to selectively move the first portion of the tab and the second portion of the tab.

20. The device of claim 19, wherein the body has a bottom surface and an upper surface, wherein the upper surface is angled with respect to the bottom surface.

21. The device of claim 19, further comprising one or more plugs, wherein the body and the tab comprise one or more holes that extend from outside the device to the interior cavity and are configured to be removably filled by the plugs.

22. The device of claim 21, wherein the plugs comprise bone material.

23. The device of claim 19, wherein the tab comprises one or more tangs positioned along a perimeter of a top surface of the tab and fit within recesses in a top surface of the body when the tab is in the retracted position.

24. The device of claim 23, wherein one or more of the tangs extend from a perimeter of the tab to a perimeter of the body.

25. The device of claim 19, wherein the second drive screw is parallel to the first drive screw.

26. The device of claim 19, wherein the second drive screw is perpendicular to the first drive screw.

* * * * *